United States Patent [19]
Holm

[11] Patent Number: 5,776,336
[45] Date of Patent: Jul. 7, 1998

[54] ANNULAR FILTER ASSEMBLY

[75] Inventor: Niels Erik Holm, Birkerød, Denmark

[73] Assignee: Bristol-Myers Squibb Company, New York, N.Y.

[21] Appl. No.: 739,663

[22] Filed: Oct. 31, 1996

Related U.S. Application Data

[60] Division of Ser. No. 421,599, Apr. 12, 1995, Pat. No. 5,603,845, which is a continuation-in-part of Ser. No. 155,984, Nov. 19, 1993, abandoned.

[51] Int. Cl.$^6$ .......................... B01D 21/26; B01D 35/00; A61K 35/16
[52] U.S. Cl. .................... 210/206; 210/338; 210/360.1; 210/380.1; 210/435
[58] Field of Search ............................. 210/198.1, 205, 210/206, 435, 338, 360.1, 380.1

[56] References Cited

U.S. PATENT DOCUMENTS

| | | |
|---|---|---|
| 3,064,647 | 11/1962 | Earl . |
| 3,078,847 | 2/1963 | Wandell et al. . |
| 3,799,342 | 3/1974 | Greenspan . |
| 3,908,893 | 9/1975 | Williams . |
| 3,911,918 | 10/1975 | Turner . |
| 3,932,277 | 1/1976 | McDermott et al. . |
| 4,086,924 | 5/1978 | Latham, Jr. . |
| 4,141,887 | 2/1979 | Seufert . |
| 4,300,717 | 11/1981 | Latham, Jr. . |
| 4,359,049 | 11/1982 | Redl et al. . |
| 4,471,888 | 9/1984 | Herb et al. . |
| 4,530,691 | 7/1985 | Brown . |
| 4,566,610 | 1/1986 | Herb . |
| 4,596,657 | 6/1986 | Wisdom . |
| 4,666,429 | 5/1987 | Stone . |
| 4,668,399 | 5/1987 | Duggins . |
| 4,729,829 | 3/1988 | Duggins . |
| 4,735,726 | 4/1988 | Duggins . |
| 4,767,396 | 8/1988 | Powers . |
| 4,784,157 | 11/1988 | Halls et al. . |
| 4,795,441 | 1/1989 | Bhatt . |
| 4,810,378 | 3/1989 | Carmen et al. . |
| 4,818,386 | 4/1989 | Burns . |
| 4,828,716 | 5/1989 | McEwen et al. . |
| 4,902,281 | 2/1990 | Avoy . |
| 4,934,827 | 6/1990 | Taschke . |
| 5,030,215 | 7/1991 | Morse et al. . |
| 5,100,372 | 3/1992 | Headley . |
| 5,137,181 | 8/1992 | Keller . |

FOREIGN PATENT DOCUMENTS

| | | |
|---|---|---|
| 0285076 | 10/1988 | European Pat. Off. . |
| 0446713 | 2/1991 | European Pat. Off. . |
| 0430355 | 6/1991 | European Pat. Off. . |
| 0505962 | 3/1992 | European Pat. Off. . |
| 3920694 | 1/1991 | Germany . |
| 2202469 | 9/1988 | United Kingdom . |
| 8802259 | 4/1988 | WIPO . |

*Primary Examiner*—David A. Reifsnyder
*Attorney, Agent, or Firm*—Theodore R. Furman, Jr.; John M. Kilcoyne; Stuart E. Krieger

[57] ABSTRACT

In a process of separating a liquid sample having phase portions of different densities by centrifugal separation, a phase separator container is employed. The phase separator container comprises a housing having concentric inner and outer cylindrical walls defining a longitudinal axis and a top wall and further a piston body constituting a bottom wall of the housing. The piston body defines together with the outer cylindrical wall, the inner cylindrical wall and the top wall, an annular chamber for receiving the liquid sample. The piston body is displaceable within the annular chamber for draining a phase portion separated from the liquid sample through a drain conduit means communicating with the annular chamber. The phase separation chamber further comprises a reaction chamber to which the phase portions exposed from the annular chamber is processed. The apparatus further includes a liquid supply means for supplying the liquid sample to the annular chamber, a motor means for rotating the phase separation container round its longitudinal axis at a rotational speed causing a separation of the liquid sample into the phase portions, and an actuator means for displacing the piston body within the annular chamber.

2 Claims, 14 Drawing Sheets

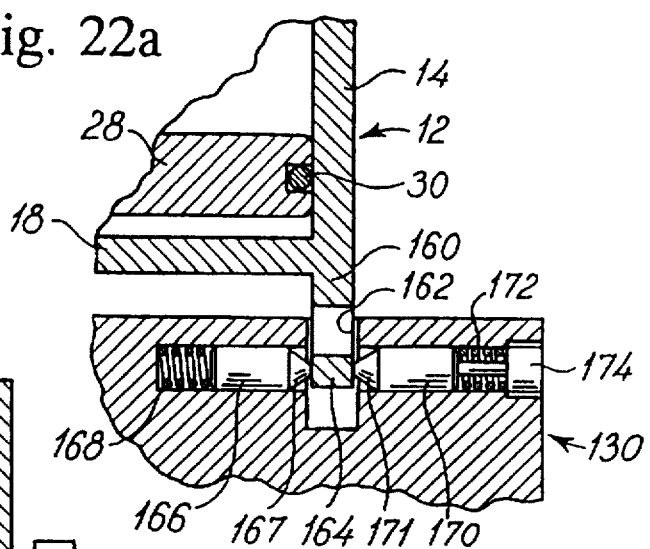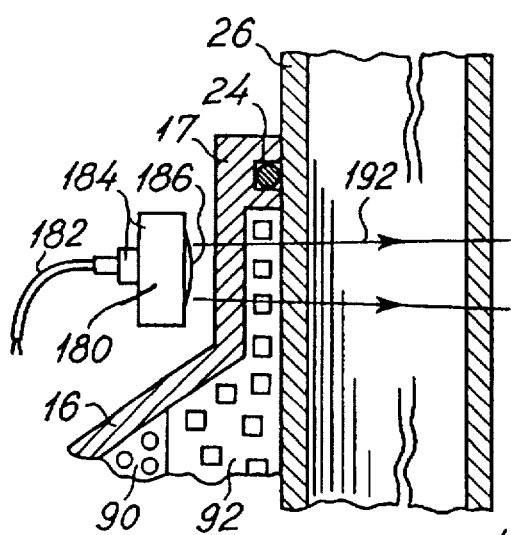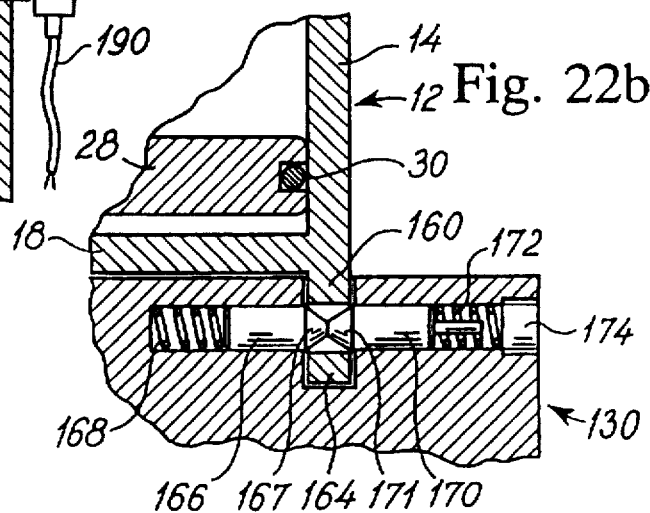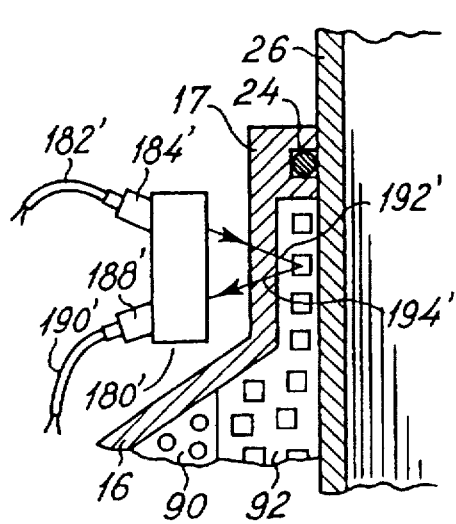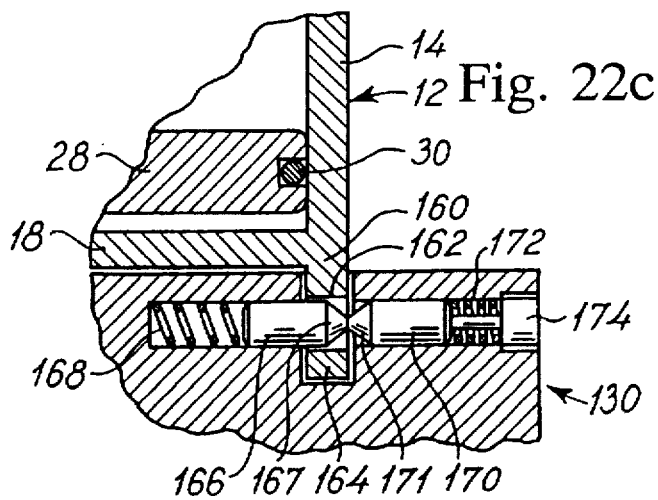

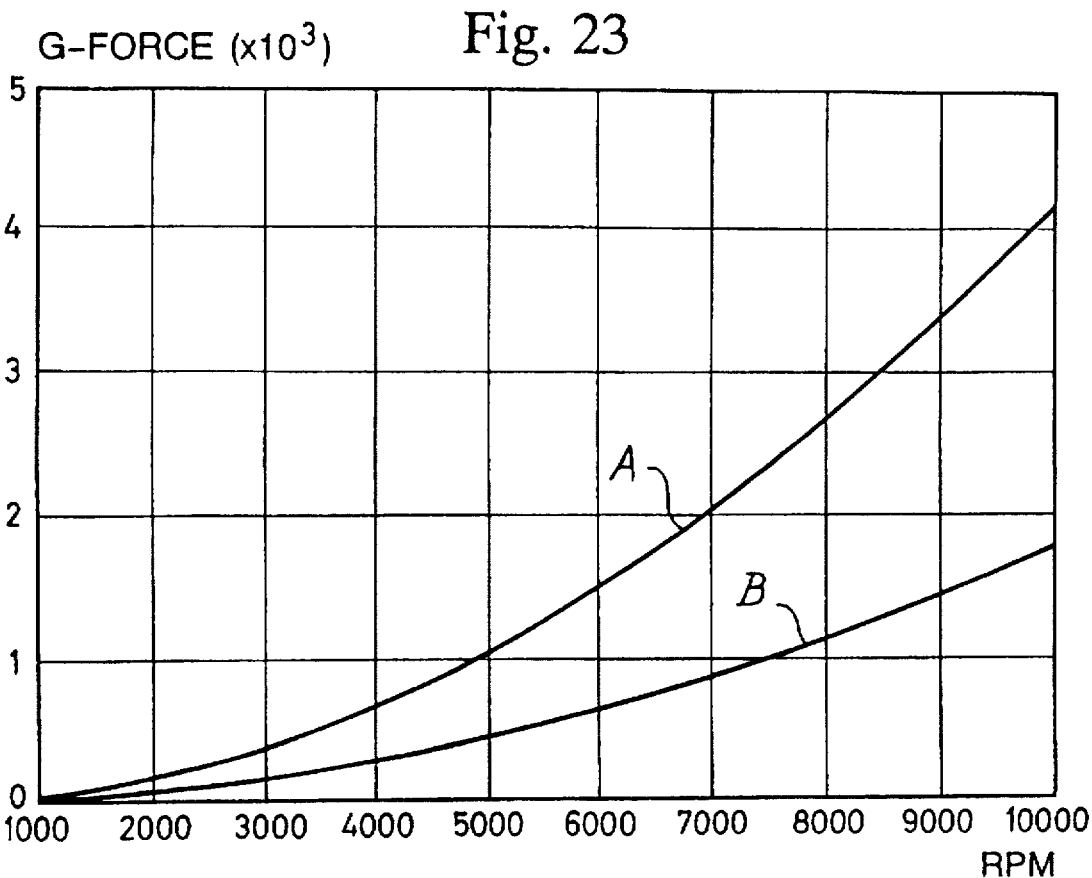
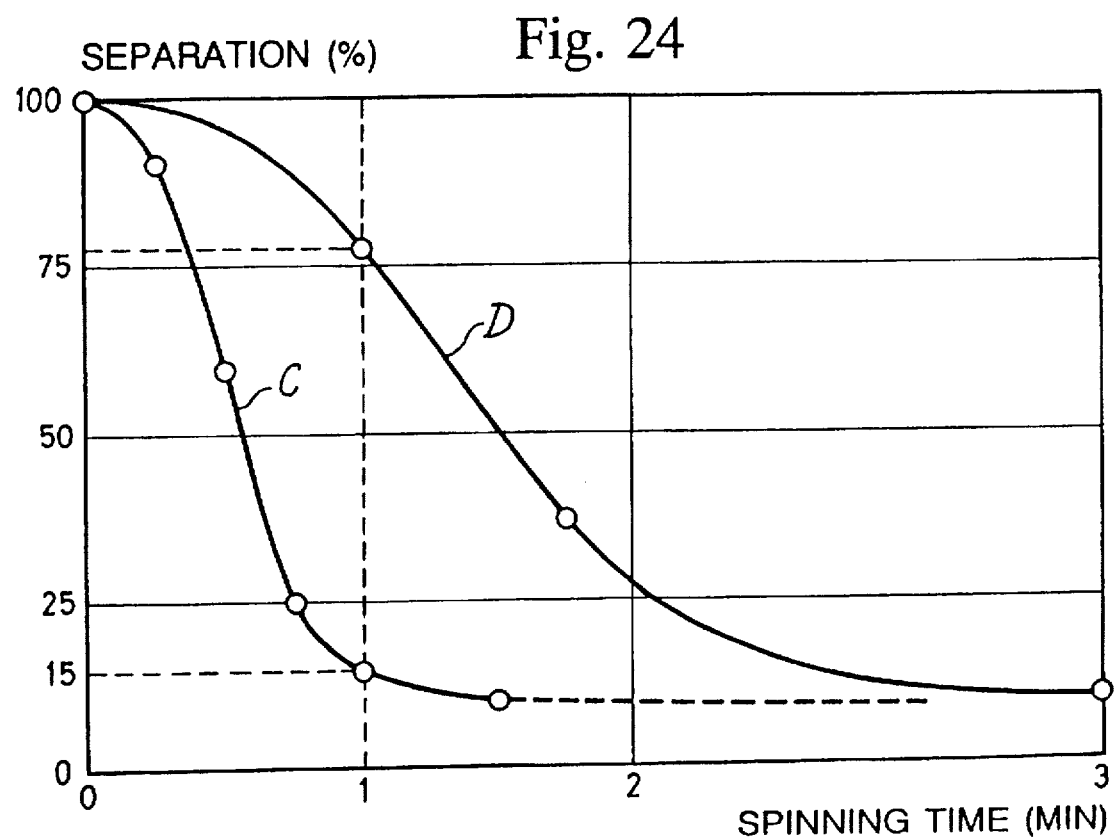

ANNULAR FILTER ASSEMBLY

This application is a divisional application of U.S. Ser. No. 08/421,599 filed Apr. 12, 1995 now U.S. Pat. No. 5,603,845 which is a continuation-in-part of U.S. Ser. No. 08/155,984 filed Nov. 19, 1993, now abandoned.

FIELD OF THE INVENTION

This invention relates to novel methods, devices and apparati for the centrifugal separation of a liquid into its components of varying specific gravities, and is more particularly concerned with a blood separation device useful, for example, in the preparation of components for a fibrin sealant.

BACKGROUND OF THE INVENTION

The separation of a liquid into its fractions, or components of varying specific gravity, has been carried out, inter alia, by centrifugation in many hospital, laboratory and industrial settings. For example, centrifugation is widely used in blood separation techniques to separate blood into fractions containing plasma, platelets, red blood cells white blood cells and/or formed components, e.g. fibrinogen, fibronectin, factor VIII, factor XIII and the like. Quite simply, devices for use in such techniques rely on the more dense components, e.g. the cell-containing fraction(s) in blood, being forced to a distal portion of the apparatus by the centrifugal force.

Many of the numerous device designs which utilize centrifugation can be placed into two categories: a first group in which the sample container is swung about a central axis of the centrifuge system itself; and, a second group in which the chamber is rotated about its own longitudinal axis. In the first category the container is typically a plastic bag or tube closed on one end. Such containers are orbited about the central axis of the centrifuge system such that the more dense components are forced to the bottom of the tube or to one side of the bag. Means are thereafter provided to selectively remove the less dense component, such as plasma from the more dense component, such as blood cells and platelets, or vice versa. Typically such means is a separator assembly which is insertable into an elongated blood-containing tube. Alternatively, when using a plastic bag, the bag is carefully squeezed so as to force out the plasma. U.S. Pat. No. 3,932,277 to McDermott et al discloses a device comprising a sample tube and a collection tube. The collection tube has a filter and check valve at one end which is inserted into an already centrifuged sample tube to collect the plasma. Similarly U.S. Pat. No. 3,799,342 to Greenspan utilizes a separator having a check valve which opens upon pressurization of the sample container to allow separated plasma to pass through into a collection chamber. U.S. Pat. No. 4,818,386 to Burns employs a semi-buoyant separator designed to have a specific gravity intermediate the specific gravities of two components into which the liquid is to be separated. Upon centrifugation, the separator moves within an elongated blood sample tube to a position substantially between the more dense materials at the bottom and the less dense materials at the top. An elastomeric cup encompassing the separator locks the separator in place when centrifugation is ceased to facilitate selective removal of the less dense component.

As mentioned, a second category includes devices wherein the liquid-containing chamber is rotated about its longitudinal axis. The liquid containing chamber is typically cylindrical or bowlshaped such that upon centrifugation heavier liquid components, e.g. blood cells, migrate outwardly toward the chamber wall and the lighter components, e.g. plasma, remain inward. Within this category are devices which include conduits to other distinct containers, typically for the receipt and/or transfer of liquid during centrifugation, and devices which are self-contained for processing a fixed volume of liquid. One such device of the former variety is the "Latham bowl" disclosed and modified in a number of patents including U.S. Pat. No. 4,086,924, 4,300,717, etc. The Latham bowl is designed such that the less dense components towards the inner portion of the spinning bowl are forced upward into a collection area inward of the outermost bowl radius. This system, however, requires a constant flow of blood to force the separated plasma out and this "flow-during-spinning" feature mandates complex and expensive rotary seals.

McEwen in U.S. Pat. No. 4,828,716 separates a liquid, such as blood, into its components, such as plasma and red blood cells, by centrifugation in an elongated tube at speeds sufficient to provide a concentric interface between these components. That is, a substantially cylindrical apparatus is spun about its central or longitudinal axis such that the more dense cellular components move to the outer wall and the less dense components are inward of the more dense components. McEwen device thereafter reduces the volume of the processing chamber and collects the less dense plasma components by forcing it to a central collection port.

The above-described concentric separation occurs, by virtue of the centrifugal, or G-force, acting upon the components, which is dependent upon radius and which can be expressed as $$G = 1.18 \times 10^{-5} \times \text{Radius (CM)} \times \text{RPM}^2$$

To provide a good separation of components, it is beneficial to provide as "sharp" an interface as possible between the components of varying density. Thus, for each liquid made up of two or more components, there is minimal G-force needed to maintain this concentric interface. One potential difficulty with such prior art reducing-volume/concentric-interface devices is that it becomes difficult to maintain the desired separation interface because as the volume is reduced and the plasma is collected, the height of the processing chamber is also decreasing. This provides, obviously, that the constant volume of cellular (more dense) material is forced inward to a decreasing radius. Indeed this must occur with the prior art device to force the plasma material centrally towards the collection port. However, it can be appreciated that when the radius of cellular material drops below the critical value needed to maintain a concentric interface at a given speed, the interface becomes much less clearly defined, if not nonexistent, and collection of unwanted cellular material results. For the McEwen-type blood separation, the volume of pure plasma is not as critical as for certain other applications. Also, the McEwen-type device operated at ultracentrifugation ranges.

In more current technologies, it has become critical to be able to separate blood components with a more reliable purity of separation resulting in a higher hematocrit value, i.e. ratio of to red blood cells to the total volume of the sample. It is also highly desirable to be able to provide separation in shorter periods of time and with minimal need for detection devices. Further, ultracentrifugation can exert excessive shear forces on blood components which have undesirable effects, e.g. hemolysis. It would be useful in many applications to provide the above liquid separation benefits, especially at centrifuge speeds below 20,000 RPM, preferably in the 3,000–15,000 RPM and optimally in the 5,000–10,000 RPM range. Typically, centrifuge speeds above about 10,000 RPM results in severe journalling and bearing problems especially relating to the problem of providing adequate lubrication.

An object of the present invention is to provide more accurate and efficient separation of liquid, in particular blood, into its phase portions of different densities through the employment of improved separation techniques. A particular advantage of the present invention is that a quick, efficient separation of liquid components can be accomplished without the disadvantages, i.e., expensive, complex equipment and damage to components such as blood components, of an ultracentrifugation system.

A particular feature of the present invention relates to the fact that in accordance with the novel separation and collection techniques according to the present invention, a blood sample may be used to provide a Fibrin extraction to be used in the preparation of a tissue repair promoting substance, a so-called tissue-glue, which separation and preparation is carried out in a field compartment eliminating the risk that laboratory persons or operators are exposed to infectious agents that may be passed through contact with blood, e.g. hepatitis or acquired immune deficiency syndrome.

A particular advantage of the present invention relates to the novel separation and collection technique which renders it possible to perform a separation of a blood sample for separating the blood sample into plasma and blood cells which separation further provides a separation of blood platelets from the blood cells and consequently provides the ability to obtain plasma with a desired high or low platelet level by varying the appropriate process parameters.

BRIEF DESCRIPTION OF THE INVENTION

The present invention provides for more accurate and efficient separation of liquid into its separate components through the employment of improved separation and collection techniques and novel devices suitable in such techniques. Separation by centrifugation to provide a concentric interface between components of a liquid is enhanced by using a cylindrical housing having fixed outer and inner cylindrical wall which with top and bottom walls, define an annular chamber. The radius of the inner cylindrical wall from the longitudinal axis of the device is chosen such that at the desired speed(s) of centrifugation there will always be a sufficient centrifugal force (G-force) maintained at the inner cylindrical wall, and thereby throughout the annular chamber, to sustain such a concentric interface of components. By reducing the volume of the annular chamber during centrifugation the desired component or compounds can be selectively removed via a drain means.

The resulting separation can be carried out relatively quickly and at relatively low speeds. By a suitable choice of the inner and outer radius of the chamber, it is possible, for example, to achieve a separation of up to 80% of the plasma of a blood sample in about 1 minute at a speed of rotation of approximately 5,000 rpm. The axially symmetrical inner wall provides that the chamber in which the separation is to be carried out is annular, which in turn ensures that the components in the chamber are always subjected to a G-force during the reduction of the volume which maintains a sharp interface. An annular chamber renders it furthermore possible in connection with a given blood sample to achieve a relatively small distance between the inner wall and the outer wall with the result that the components to be separated from one another need only move a relatively short distance. Accordingly, the separation is carried out quickly with a relatively high purity of the individual components.

The above object, the above feature and the above advantage together with numerous other objects, advantages and features which will be evident from the below description of presently preferred embodiments of the present invention are in accordance with the first aspect of the present invention obtained by an apparatus for separating a liquid sample having phase portions of different densities into said phase portions by centrifugal separation, comprising:

a phase separation container, comprising:

a housing having concentric inner and outer cylindrical walls defining a longitudinal axis, a bottom wall, and a top wall, said outer cylindrical wall, said inner cylindrical wall, said bottom wall and said top wall defining together an annular chamber for receiving said liquid sample, a piston body constituting said bottom wall or top wall of said housing and being displaceable within said annular chamber from a first position in which a maximum interior volume is defined within said annular chamber to a second position in which a minimum interior volume is defined within said annular chamber, and a drain conduit means communicating with said annular chamber, a liquid supply means for supplying said liquid sample to said annular chamber of said phase separation chamber as said piston body is in said first position, a motor means for rotating said phase separation container round said longitudinal axis at a rotational speed causing a separation of said liquid sample into said phase portions, an actuator means for displacing said piston body within said annular chamber from said first position towards said second position while said phase separation container is rotated at said rotational speed so as to expel one of said phase portions from said annular chamber through said drain conduit means.

The above object, the above feature and the above advantage together with numerous other objects, advantages and features which will be evident from the below description of presently preferred embodiments of the present invention are in accordance with the second aspect of the present invention obtained by a phase separation container to be used in an apparatus for separating a liquid sample having phase portions of different densities into said phase portions by centrifugal separation, said phase separation container comprising:

a housing having concentric inner and outer cylindrical walls defining a longitudinal axis, a bottom wall, and a top wall, said outer cylindrical wall, said inner cylindrical wall, said bottom wall and said top wall defining together an annular chamber for receiving said liquid sample, a piston body constituting said bottom wall or top wall of said housing and being displaceable within said annular chamber from a first position in which a maximum interior volume is defined within said annular chamber to a second position in which a minimum interior volume is defined within said annular chamber, and a drain conduit means communicating with said annular chamber.

A third aspect of the present invention involves a cylindrical receiver chamber for receiving the phase portions expelled from the annular chamber and separated from the annular chamber by the piston body.

A fourth aspect of this invention pertains to the apparatus and phase separation container as above wherein the inner cylindrical wall of the annular chamber is a cylindrical wall component of the piston body.

A fifth aspect of the invention involves methods for using the above apparatus for separation of a liquid into phase portions of different densities.

A sixth aspect of the invention relates to such a method wherein the ration $(r_i : r_o)$ of the radius of the inner wall $r_i$ to the radius of the outer wall $r_o$ is between about 0.3:1 and about 0.8:1 preferably 0.5:1.

A seventh aspect of the invention involves the apparatus and phase separation container as described above including connector means connecting the phase separation container to the motor means.

The above object, the above feature and the above advantage together with numerous other objects, advantages and features which will be evident from the below description of presently preferred embodiments of the present invention are in accordance with another aspect of the present invention obtained by a method of separating a liquid sample having phase portions of different densities into said phase portions by centrifugal separation, said method comprising:

providing a phase separation container, comprising:
  a housing having concentric inner and outer cylindrical walls defining a longitudinal axis, a bottom wall, and a top wall, said outer cylindrical wall, said inner cylindrical wall, said bottom wall and said top wall defining together an annular chamber for receiving said liquid sample,
  a piston body constituting said bottom wall or top wall of said housing and being displaceable within said annular chamber from a first position in which a maximum interior volume is defined within said annular chamber to a second position in which a minimum interior volume is defined within said annular chamber, and
  a drain conduit means communicating with said annular chamber,
supplying said liquid sample to said annular chamber of said phase separation chamber as said piston body is in said first position,
rotating said phase separation container round said longitudinal axis at a rotational speed causing the generation of a gravitational field within said annular chamber so as to separate said liquid sample into said phase portions at any location within said annular chamber,
displacing said piston body within said annular chamber from said first position towards said second position while said phase separation container is rotated at said rotational speed so as to expel one of said phase portions from said annular chamber through said drain conduit means.

The above object, the above feature and the above advantage together with numerous other objects, advantages and features which will be evident from the below description of presently preferred embodiments of the present invention are in accordance with another aspect of the present invention obtained by a method of separating a liquid sample having phase portions of different densities into said phase portions by centrifugal separation, said method comprising:

providing a phase separation container, comprising:
  a housing having concentric inner and outer cylindrical walls defining a longitudinal axis, a bottom wall, and a top wall, said outer cylindrical wall, said inner cylindrical wall, said bottom wall and said top wall defining together an annular chamber for receiving said liquid sample,
  a piston body constituting said bottom wall or top wall of said housing and being displaceable within said annular chamber from a first position in which a maximum interior volume is defined within said annular chamber to a second position in which a minimum interior volume is defined within said annular chamber, and
  a drain conduit means provided at or near said inner cylindrical wall and communicating with said annular chamber,
supplying said liquid sample to said annular chamber of said phase separation chamber as said piston body is in said first position,
continuously rotating said phase separation container round said longitudinal axis at a rotational speed causing one of said phase portions to be separated from said liquid sample, and
displacing said piston body within said annular chamber from said first position towards said second position while said phase separation container is rotated at said rotational speed so as to continuously expel said one of said phase portions from said annular chamber through said drain conduit as said one of said phase portions is separated from said liquid sample.

The above object, the above feature and the above advantage together with numerous other objects, advantages and features which will be evident from the below description of presently preferred embodiments of the present invention are in accordance with another aspect of the present invention obtained by an apparatus for separating a liquid sample having phase portions of different densities into said phase portions by centrifugal separation, further including:

means for detecting the characteristics of one or both of the components within said phase separation container during the separation process.

The methods according to the above aspects of the present invention like the apparatus and the container according to the other aspects of the present invention, are preferably used for separating plasma from a blood sample. Thus, the apparatus, the phase separation container and the method according to the present invention are advantageously and preferably used for separating a blood sample into various constituents such as blood cells and plasma optionally including platelets or alternatively constituting platelet-free plasma.

Most preferably the apparatus and methods are employed to prepare a composition containing fibrin monomer or non-crosslinked fibrin, optimally for use in a fibrin sealant.

DETAILED DESCRIPTION OF PREFERRED EMBODIMENTS

The present invention will now be further described with reference to the drawings, in which FIG. 1 is a schematic and sectional view of a first embodiment of a sample container of a centrifugal separation and processing apparatus implemented in accordance with the teachings of the present invention.

FIGS. 22a–22c are schematic and sectional views of a mechanism for arresting and fixating the sample container relative to the centrifuge separation and processing apparatus, illustrating three steps of the arresting and fixating process.

FIGS. 22d and 22e are schematic and sectional views of a lid component of the sample container communicating with optical detectors implemented in accordance with two alternative optical detector principals.

FIG. 23 is a diagrammatic view illustrating the dependency between the gravitational force at the inner and outer walls of the phase separation chamber of the sample container and the rotational speed of the sample container.

FIG. 24 is a diagrammatic view illustrating the yield percentage of a specific blood sample when separating the blood sample by means of the sample container according to the present invention in dependency of the time of performing the separation process further illustrating two specific yield curves corresponding to the yield of plasma of high and low blood platelets content, respectively.

DETAILED DESCRIPTION OF THE DRAWINGS

Figure 1:
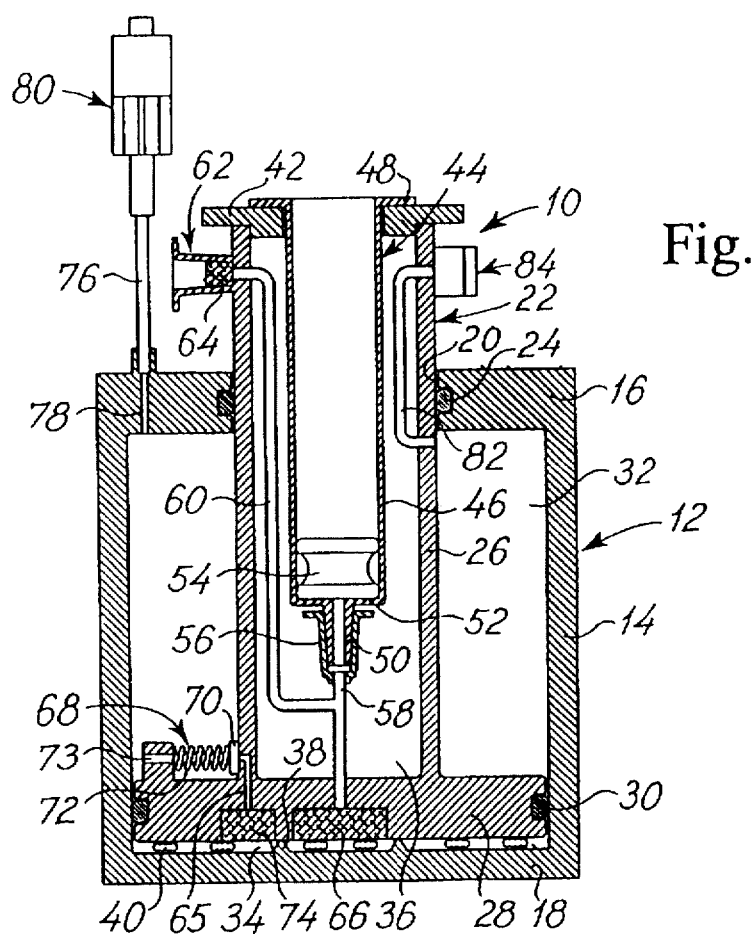

In FIG. 1, a first embodiment of a sample container implemented in accordance with the teachings of the present invention is shown designated the reference numeral 10 in its entirety. The sample container 10 constitutes a unitary structure to be used in a centrifugal separation and processing apparatus to be described below. Although the invention herein is described throughout in terms of blood separation, preferably for the preparation of components suitable for a fibrin glue, it should be appreciated that the devices, apparati and methods herein can be employed with any liquid separation application. The present invention is particularly suited for the separation of a blood sample into blood cells and plasma and for preparing a Fibrin extract from the plasma, e.g. in accordance with the technique described in international patent application, application No. PCT/DK87/00117, publication No. Wo 88/02259, and European Application No. EP 592,242 entitled *FIBRIN SEALANT COMPOSITIONS AND METHODS FOR UTILIZING SAME* filed Oct. 18, 1993.

In EP 592,242 methods and compositions for a completely novel fibrin glue are disclosed. Generally, EP 592, 242 discloses a method of forming a fibrin sealant comprising contacting a desired site with a composition containing fibrin monomers and converting this monomer to a fibrin polymer concurrently with the contacting step, thereby forming the sealant at the desired site. The term fibrin is understood to include fibrin I, fibrin II and des BB fibrin. EP 592,242 further discloses a method of forming a fibrin monomer composition comprising the steps of:

a) contacting a composition containing fibrinogen with a thrombin-like enzyme to form a non-crosslinked fibrin polymer;

b) separating the non-crosslinked fibrin polymer from the fibrinogen composition, and c) solubilizing the non-crosslinked fibrin polymer to provide a composition containing fibrin monomer.

The thrombin-like enzyme can be thrombin itself or can be another enzyme with similar activity, e.g., Ancrod, Acutin, Venzyme, Asperase, Botropase, Crotalase, Flavoxobin, Gabonase, or Batroxobin, with Batroxobin being preferred.

In accordance with a preferred embodiment of the present invention, the earlier-disclosed fibrin monomer preparation can be carried out in a rapid, efficient and safe manner in a unitary two-(or more) chamber device. The present device provides for such fibrin monomer preparation in less than 30 minutes and is especially useful in single donor or preferably autologous fibrin sealant preparations. The single donor or autologous fibrin monomer composition can be co-administered with an alkaline buffer or distilled water preferably including a source of calcium ions.

The sample container 10 comprises a housing 12 composed of a cylindrical wall component 14, a top wall component 16 and a bottom wall component 18. The top wall component 16 is provided with a central through-going aperture 20 in which a piston component 22 extends and seals relative to the central through-going aperture 20 of the top wall component typically by means of an O-ring sealing 24.

The wall components 14, 16 and 18 are joined together after the piston component 22 is received within the central through-going aperture 20 of the top wall component 16, by any convenient means, e.g. by means of meshing threads or by gluing the wall components together. Thus, the cylindrical wall component 14 and the bottom wall component 18 may constitute an integral structure which is connected e.g. by glue or by means of meshing threads to the top wall component 16. Alternatively, the top wall component 16 and the cylindrical wall component may constitute an integral structure which is connected to a separate bottom wall component. Further alternatively, the wall components 14, 16 and 18 may constitute three separate components which are joined together by means of meshing threads or in any other appropriate matter, e.g. by gluing or welding the wall components together.

As can be seen the inner cylindrical wall 26 and the outer cylindrical wall 14 define the annular chamber in which centrifugation takes place. The radii of these walls from the longitudinal axis of the container 10 are chosen so that at the desired speeds of rotation a sufficient G-force is created to maintain concentric separation of the liquid components. Of course, this will vary depending upon the liquid and the desired speeds. For separating blood, for example, a G-force of about 400 to about 1000 G should be maintained using the present apparatus. This provides that for speeds of about 5,000–10,000 RPM, preferably about 5,000 RPM, the radius of the inner cylindrical wall 26 is typically at least about 1.0 to about 1.5 cm depending upon the speed and blood sample. The radius of the outer cylindrical wall can vary accordingly depending upon the sample size to be accommodated. Outer radii of about 2.0 to about 3.5 cm and above are suitable for separating blood components in the 5,000–10,000 RPM range. Preferably the ratio of inner wall radius $r_i$ to outer wall radius $r_o$ is from about 0.3:1 to about 0.8:1 and most preferably about 0.5:1.

The piston component 22 comprises a cylindrical wall component 26 which seals against the above mentioned O-ring sealing 24. The cylindrical wall component 26 is integrally connected to a circular plate component 28, which is sealed relative to the inner surface of the cylindrical wall component 14 by means of an O-ring sealing 30. The O-ring sealings 24 and 30 allow that the piston component 22 may be raised and lowered relative to the housing 12 for varying the inner chambers defined within the sample container 10 as will be explained in greater detail below and for sealing the inner chambers relative to one another and relative to the environment.

The piston component 22 basically can define one, two or three chambers within the housing 12 of the sample container 10, vis a-vis first chamber 32 which is of a basically annular configuration defined between the cylindrical wall components 14 and 26, an optional second chamber defined between the bottom wall component 18 and the circular plate component 28, and an optional third chamber 36 defined within the cylindrical wall component 26 of the piston body 22.

From the inner surface of the bottom wall component 18, an optional protrusion 38 constituted by one or more separate cam elements or a circular protrusion extends upwardly so that the inner volume of the second chamber 34 is not reduced to zero. Within the second chamber 34 may be included a desired first chemical or biochemical agent 40 in any form which can be used to treat or interact with a liquid component separated in the first chamber 32 and extracted into the second chamber 34.

The piston component 22 can optionally be further provided with an annular lid component 42 which serves the purpose of receiving and supporting an optional syringe 44. The syringe 44 can basically be a conventional disposable syringe comprising a cylindrical housing 46. The syringe 44 as described below in this preferred embodiment is useful for introducing a desired second chemical or biochemical agent or solution into said second chamber 34. Alternatively, the syringe 44 may be substituted by an ampulla or a syringe of a somewhat different structure and configuration for complying with specific requirements such as requirements relating to mechanical compatibility relative to a dispenser or syringe assembly in which the ampulla or the syringe is to be used. At the uppermost end of the cylindrical housing 48, an outwardly protruding annular flange 48 is provided and at the lowermost end of the cylindrical housing 46 a conical end tube 50 is provided which is connected to the cylindrical outer wall of the cylindrical housing 46 through a bottom wall 52 of the cylindrical housing 46. Within the cylindrical housing 46, a plunger body 54 is received.

Figure 2:
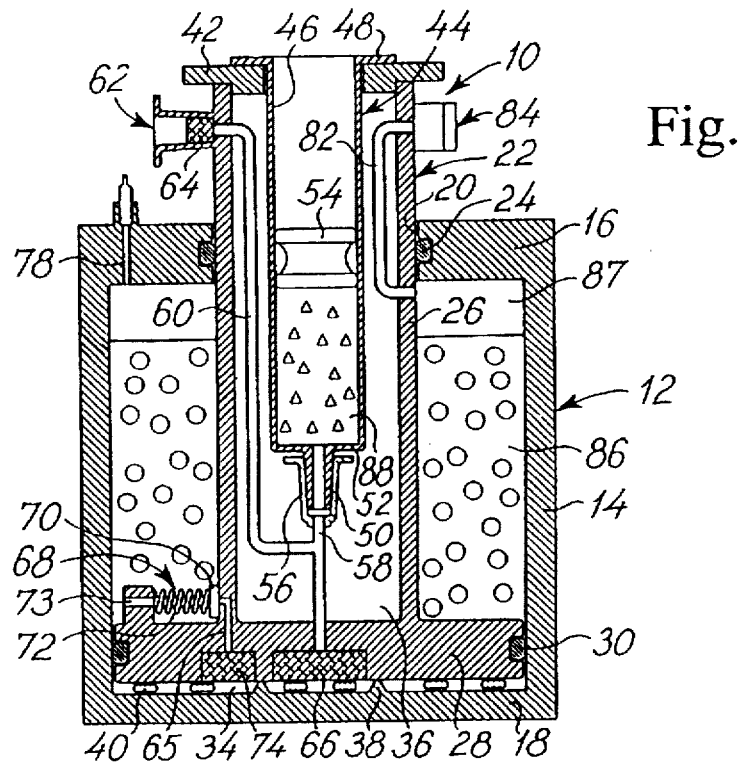
FIGS. 2–10 are schematic and sectional views similar to the view of FIG. 1 illustrating specific steps of a separation and extracting process when employing the first embodiment shown in FIG. 1.

The conical end tube 50 can be received within a conical adaptor 56 which communicates at its lower end with a tubing 58. The tubing 58 can be of a substantial length as illustrated by the signature of the tubing 58 allowing that the syringe 44 may be removed from the interior of the third chamber 36 without disconnecting the conical end tube 50 of the syringe 44 from the conical adaptor 56. The tubing 58 extends through a central bore of the circular plate component 28 into the second chamber 34 and communicates through a branch piece with a further tubing 60. The tubing 60 communicates with an inlet 62 provided at the uppermost end of the cylindrical wall component 26 of the piston component 22 at which outlet a filter element 64 is provided. The tubing 60 constitutes an inlet tubing through which a second chemical or biochemical agent 88 shown in FIG. 2 is introduced into an inner space defined within the cylindrical housing 46 of the syringe 44 which inner space is defined below the plunger body 54 as the plunger body is raised from a position shown in FIG. 1 to the position shown in FIG. 2. After the introduction of the agent 88 into the inner space of the syringe 44, the inlet 62 is preferably sealed by means of a sealing cap, not shown on the drawing. Alternatively, the inlet 62 may serve as a venting outlet for venting any excess air of the tubing 58 and the tubing 60 into the atmosphere in the process to be described below with reference to FIGS. 2–10.

The communication from the second chamber 34 to the tubing 58 may include a microporous filter means 66 which is received within a recess provided in the circular plate component 28 at the lower side surface thereof. A desired biochemical or chemical agent can also be immobilized or adsorbed onto said filter means 66 or elsewhere within said tubing 58 to treat a first liquid component which is separated in the first chamber 32 and extracted therefrom. From the first chamber 32 communication is established to the second chamber 34 through a conduit 65 which is established extending through the cylindrical wall component 26 and the circular plate component 28 of the piston component 22. It is to be realized that the conduit 65 is shown provided at a radial position within the outer surface of the cylindrical wall component 26. The conduit 65 can optionally be provided elsewhere in the upper surface of the piston plate 28 within the first chamber 32 according to which liquid components are desired to be collected. The conduit 65 is normally closed by means of a check valve 68 which may comprise a sealing plug body 70 and a spring 72 journalled on a supporting stem 73 and biasing the sealing plug body 70 toward a sealing or closing position. Preferably, the check valve 68 is positioned as close as possible relatively to the longitudinal axis of the sample container 10. Thus, in an alternative or modified embodiment of the sample container 10, the check valve 68 is enclosed within a separate sub-chamber positioned within the third chamber 36 and separated from the third chamber 36 through a separate wall component and further communicating with the first chamber 32 through a conduit extending through the cylindrical wall component 26 of the piston body 22. Alternatively, the check valve 68 may be housed within a separate recess provided within the circular plate component 28. The communication through the conduit 65 into the second chamber 34 is established through a further microporous filter element 74 similar to the microporous filter element 66 described above. The microporous filter element 74 is received within the recess provided at the lower side surface of the circular plate component 28 of the piston component 22.

The first chamber 32 further communicates with a supply tubing 76 through a bore 78 provided at the top wall component 16 of the housing 12. The supply tubing 76 can be at its outer end provided with an adaptor for receiving a needle of a syringe (not shown in the drawings) containing a sample, preferably a blood sample to be introduced into the first chamber 32 of the sample container 10.

The first chamber 32 preferably communicates with the environment through a venting tubing or conduit 82 establishing communication from the interior of the first chamber 32 to a venting outlet 84 provided opposite to the outlet 62 discussed above. The communication from the first chamber 32 through the venting tubing or conduit 82 is generally established provided the piston component 22 is in the lowermost position as shown in FIG. 1 as the inlet to the venting tubing or conduit 82 is raised above the O-ring sealing 24 provided the piston component 22 is raised to a position as shown in, e.g., FIG. 4.

Alternatively, vent means can be provided at any convenient location with said container 10.

The sample container 10 is as mentioned above preferably used for separating a blood sample into blood cells and plasma having a high content of platelets or alternatively a low content of platelets and further for extracting a blood constituent from the plasma as will be described below with reference to FIGS. 2–10.

In FIG. 2, a first step of a first process of separating a blood sample 86 into specific liquid components and of separating a blood constituent from one of the liquid components is shown.

In FIG. 2, a blood sample 86 is contained within the first chamber 32 and filling out a specific volume of the first chamber 32 providing a residual air space 87 above the blood sample 86. In a preferred embodiment, the blood sample in the first chamber 32 is in the presence of an anticoagulant. Any anticoagulant can be employed, and suitable examples include heparin, EDTA, hirudin, citrate and other calcium chelators such as NTA, HEEDTA, EDDHA, EGTA, DTPA, DCTA, HEPES, HIMOA, etc. The blood sample 86 contained within the first chamber 32 is designated by the plurality of small circles. Above the blood sample 86, an air space 87 is provided. In FIG. 2, the plunger body 54 of the syringe 44 is raised and the redissolving buffer agent 88, which can be, e.g., a redissolving buffer solution and which has preferably been introduced into the interior of the syringe 44 as described above through the tubing 60, is confined within the interior of the syringe 44. The piston component 22 of the sample container 10 is in its lowermost position allowing that the first chamber 32 is vented through the venting tubing or conduit 82 as the blood sample 86 is introduced into the first chamber 32. The redissolving buffer 88 is designated by a plurality of small triangles.

The redissolving buffer agent 88 can be any acid buffer solution preferably those having a pH between 1 and 5. Suitable examples, include acetic acid, succinic acid, glucuronic acid, cysteic acid, crotonic acid, itaconic acid, glutonic acid, formic acid, aspartic acid, adipic acid and salts of any of these. Succinic acid, aspartic acid, adipic acid and salts of acetic acid, e.g., sodium acetate are preferred. Also, the solubilization may also be carried out at a neutral pH by means of a chaotropic agent. Suitable agents include urea, sodium bromide, guanidine hydrochloride, KCNS, potassium iodide and potassium-bromide. Concentrations and volumes of such acid buffer or such chaotropic agent are as described in EP 592.242.

Figure 3:
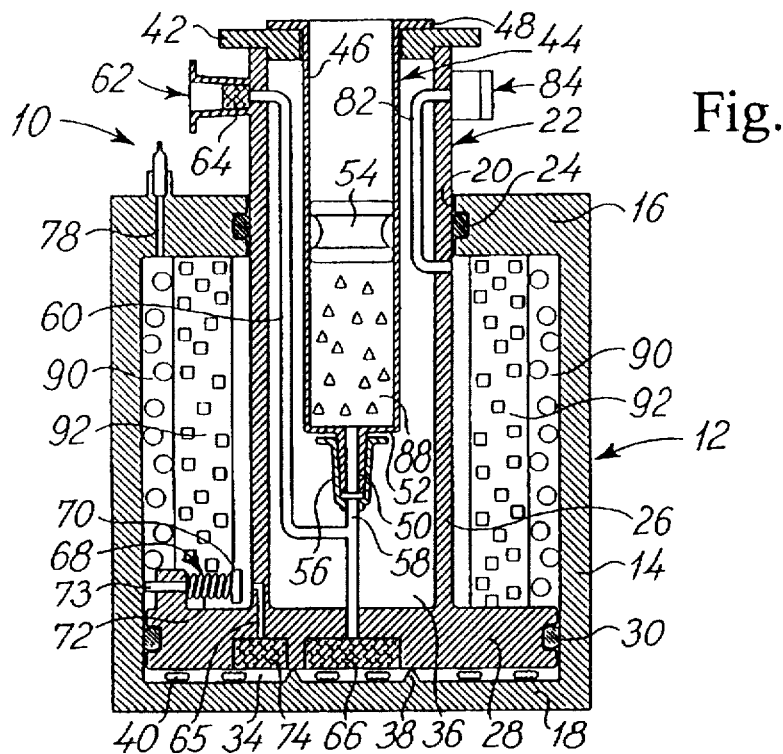

In FIG. 3, a second step of the first process is shown as the entire sample container 10 is rotated round the central longitudinal axis of the sample container 10. It is to be realized that the overall structure of the sample container 10 is of a basically symmetrical configuration as is evident from FIG. 1. It is further to be realized that the blood sample contained within the first chamber 32 is exposed to a basically constant centrifugal force of the order of 500–1,000 G as the first chamber is of an overall annular configuration of a fairly small radial variation and as the sample container 10 is rotated at a rotational speed of approximately 5,500 RPM. In FIG. 3, the blood sample contained within the first chamber 32 is separated into two components, a liquid 90 containing blood cells and designated by the above described circles, and plasma 92 designated by a plurality of small squares. The liquid 90 containing blood cells is of a somewhat higher density than the plasma 92 causing a separation due to the high rotational speed generated as the sample container 10 is rotating at a rotational speed of 5–10,000 rpm.

As the sample container 10 is rotated at the above mentioned rotational speed, the check valve 68 is opened as the sealing plug body 70 is forced radially outwardly. Although the check valve 68 opens, the liquid contained within the first chamber 32 does not flow through the conduit 65, as on the one hand the liquid which is separated into the liquid 90 and the liquid 92 is forced radially outwardly towards the cylindrical wall component 14 and as on the other hand the conduit 65 as pointed out above, is provided at a radial position within the cylindrical wall component 26. While the sample container 10 is still rotating, the piston component 22 is in a third step of the first process raised from the position shown in FIG. 3 to the position shown in FIG. 4 causing a transfer of liquid from the first chamber 32 to the second chamber 34.

Figure 4:
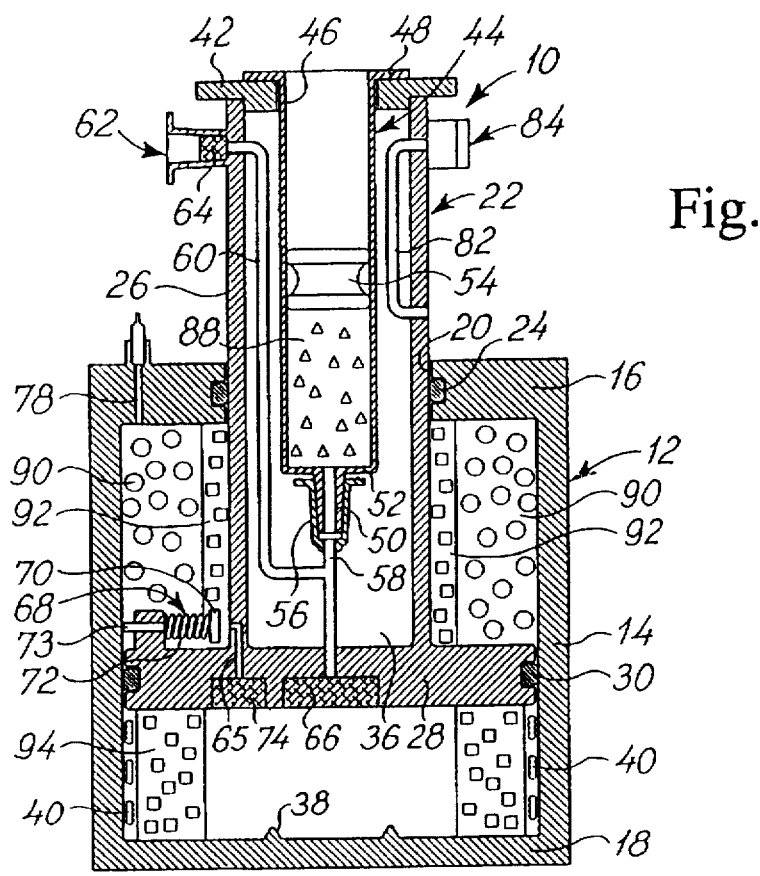

During the initial raising of the piston component 22, the air contained within the first chamber 32 is vented through the venting tubing or conduit 82. After the venting tubing or conduit 82 is raised above the O-ring sealing 24 any excess air of the air space 87 above in FIG. 2 of the first chamber 32 is transferred to the second chamber 34 as any columetric differences between the first chamber 32 and the second chamber 34 are equalized through the venting tubing 60 communicating with the second chamber 34 through the microporous filter 66. The plasma 92 shown in FIG. 3 is also transferred from the first chamber 32 to the optional second chamber 34 through the conduit 65. In FIG. 4, the plasma transferred to the second chamber 34 is designated the reference numeral 94 and shown by squares as discussed above. As the volume of the second chamber 34 is increased, the optional chemical or biochemical agent 40 are also shifted from their positions shown in FIGS. 2 and 3 to positions at the inner cylindrical surface of the enlarged second chamber 34. The agent 40, as discussed above, can be in any form, for example, an agent or enzyme can be adsorbed or immobilized onto a particulate substrate such as an enzyme bound to agarose gel or other such particles.

After a predetermined amount of plasma has been transferred from the first chamber 32 to the second chamber 34 or after substantial all plasma has been transferred from the first chamber to the second chamber 34, the raising of the piston component 22 is stopped. It is to be realized that the microporous filter element 74 prevents that any particles such as blood cells may be transferred from the first chamber 32 to the second chamber 34 in case the piston component 22 is raised above a position in which the plasma 92 has all been transferred from the first chamber 32 to the second chamber 34. It is further to be realized that the transfer of liquid from the first chamber 32 to the second chamber 34 and particular the state in which the plasma has been transferred and the first chamber 32 contains blood cells exclusively is easily detected by detecting the force which is employed for raising the piston component 22 as the force required for transferring the blood cells from the first chamber 32 to the second chamber 34 through the microporous filter element 74 is far higher than the force required for raising the piston component 22 causing the transfer of the plasma from the first chamber 32 to the second chamber 34. The transfer of all plasma from the first chamber 32 to the second chamber 34 is consequently easily detected as a radical increase in the force required for further displacing the piston component 22.

Figure 5:
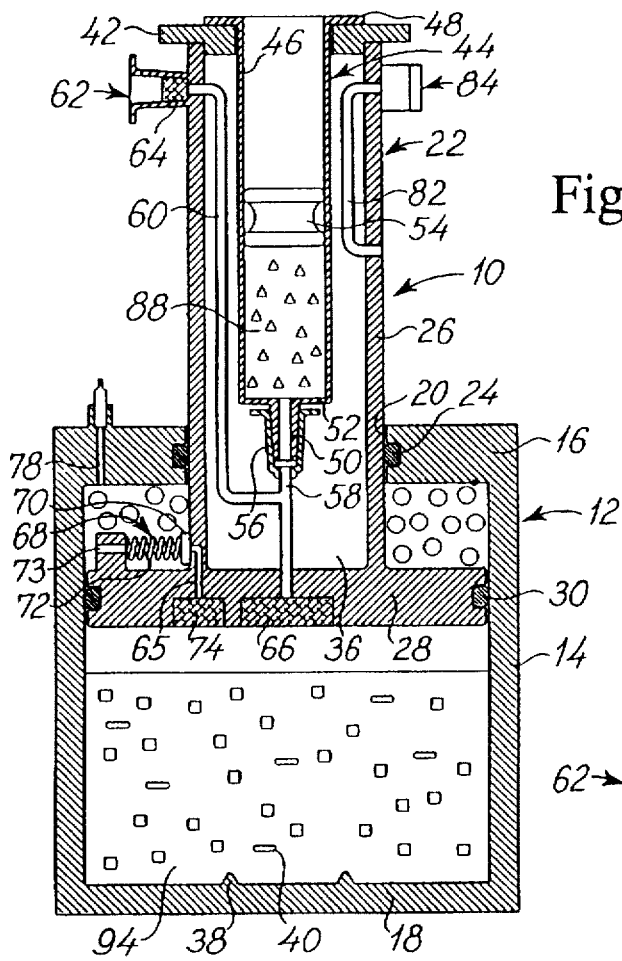

Thereupon, in a fourth step of the first process the rotation of the sample container 10 is stopped as shown in FIG. 5. In FIG. 5, the suspension of the agent 40 within the plasma 94 contained in the second chamber 34 is allowed to react for a predetermined period of time. For example, an enzyme, e.g., Batroxobin, converts the fibrinogen from the plasma into fibrin monomer which almost instantaneously polymerizes into a non-crosslinked fibrin polymer typically in the form of a gel as is more clearly described in the aforementioned EP 592,242.

Figure 6:
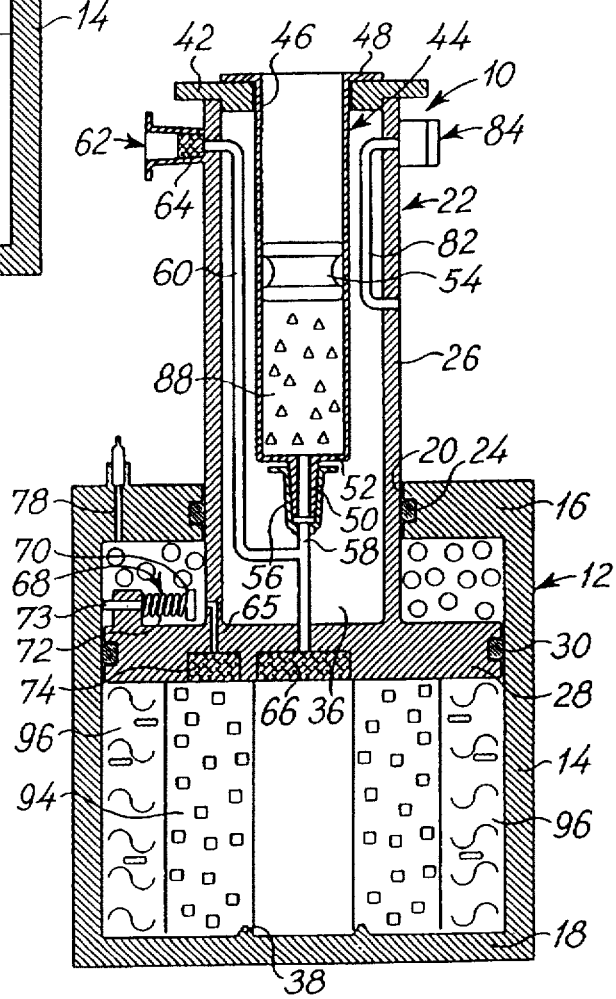
Figure 7:
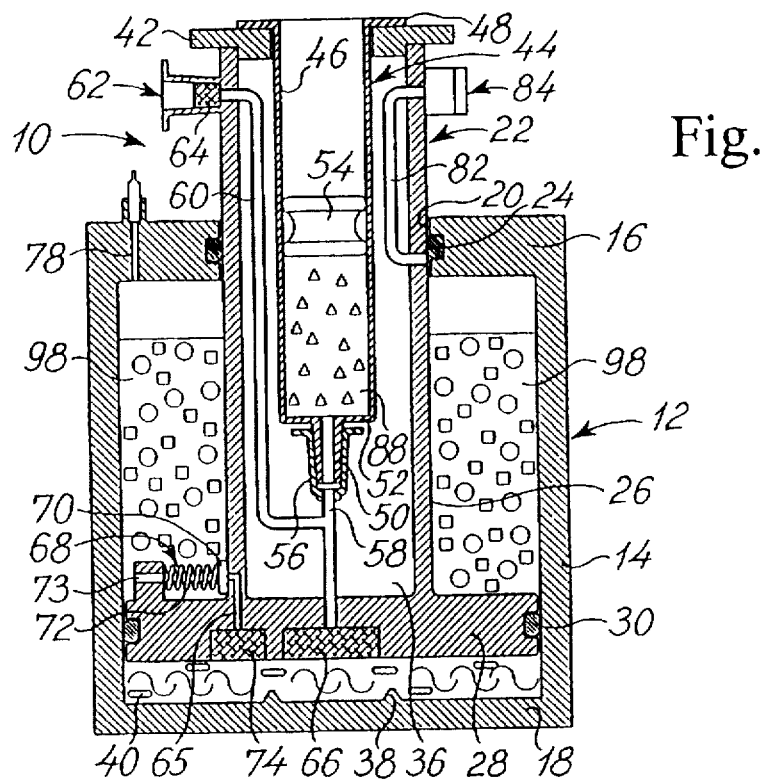
Figure 8:
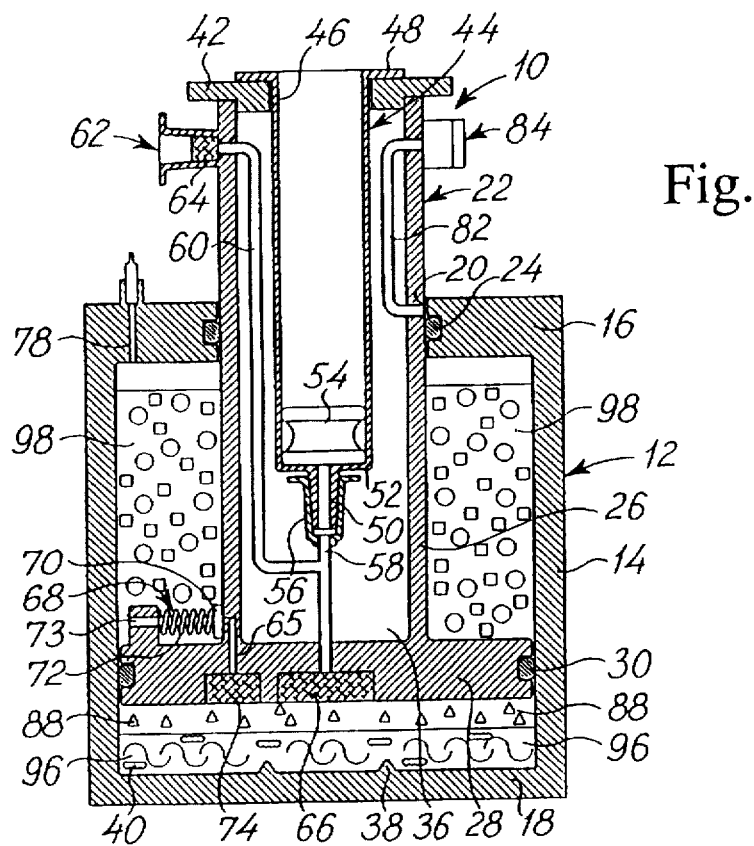

In a fifth and sixth step of the first process shown in FIGS. 6 and 7, respectively, the non-crosslinked fibrin polymer and the Batroxobin immobilized in Agarose gel particles 40 and designated by a plurality of small waves is separated from the plasma 94 contained within the second chamber 34. The second chamber 34 may also contain an inner cylindrical wall so as to provide that the second chamber 34 is also annular. In FIG. 6, the sample container 10 is in the fifth step of the first process rotated at a rotational speed causing a separation of a phase 96 containing the non-crosslinked fibrin polymer gel and the bodies 40 from the plasma 94. The rotational speed at which the sample container 10 is rotated in the fifth step of the first process can be any speed but is conveniently in this process is somewhat lower than the afore-used rotational speed at which the sample container 10 is rotated in the second step of the first process as described above with reference to FIG. 3, such as a rotational speed of approximately 0.5 times the above rotational speed, i.e. a rotational speed of the order of 2,500 RPM–3,000 RPM or lower. After the separation of the gel/particle phase 96 from the plasma 94 contained within the second chamber 34, the piston component 22 is in the sixth step of the first process lowered causing a transfer of the plasma 94 from the second chamber 34 through the conduit 65 to the first chamber 32 as the check valve 68 is opened. It is to be realized that the microporous filter element 74 prevents that any particles or larger bodies such as the agent particles 40 may be transferred from the second chamber 34 through the conduit 65 to the first chamber 32 as the microporous filter element 74 simply blocks the transfer of particles or bodies.

After the completion of the second centrifugal separation and second plasma transfer step, the second chamber 34 solely contains the liquid 96 including the non-crosslinked fibrin polymer and the agent particles 40 as shown in FIG. 7. Within the first chamber 32, a mixture 98 of liquid containing the blood cell and the plasma retransferred from the second chamber 34 is contained as indicated by the combined symbols of circles and squares.

In FIG. 7 the redissolving buffer 88 is in a seventh step of the first process added from the syringe 44 to the second chamber 34 by lowering the plunger body 52 of the syringe 44 and simultaneously raising the piston body 28 in order to provide a complete transfer of the redissolving buffer 88 from the syringe 44 to the second chamber 34 and preventing that the redissolving buffer 88 is forced into the branch piece of the tubing 58 and further into the venting tubing 60.

Figure 9:
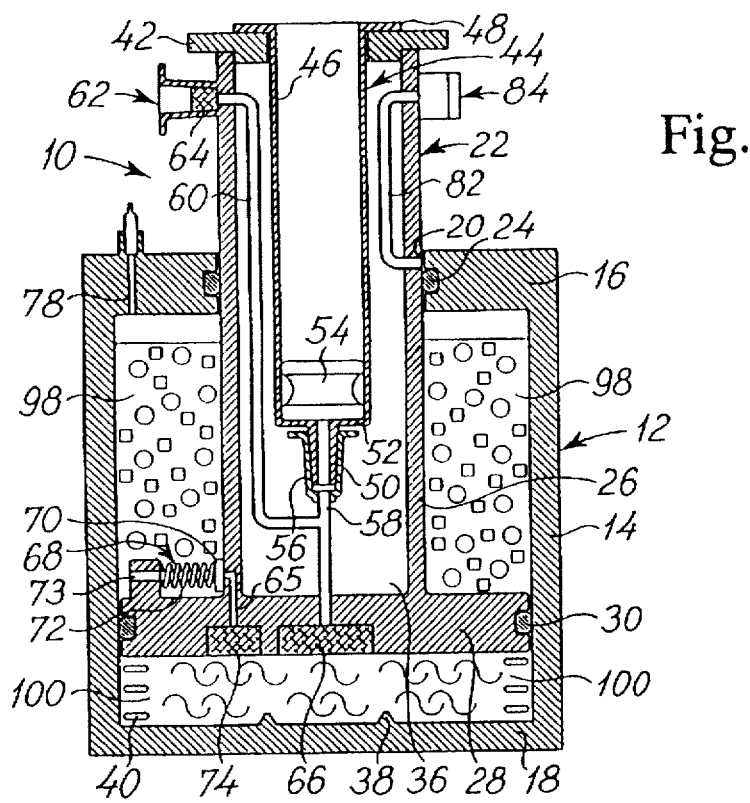
Figure 10:
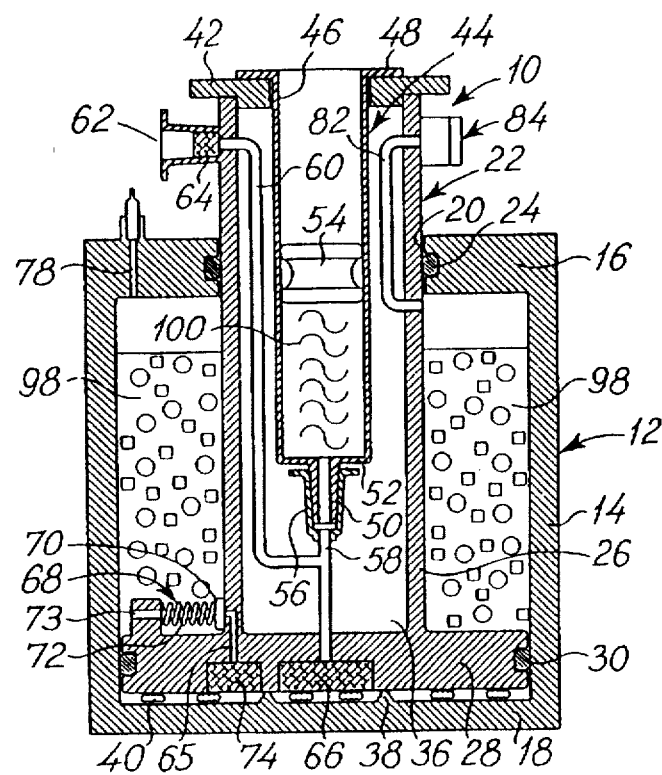

After a certain period of time during which the redissolving buffer 88 causes the dissolving of the non-crosslinked fibrin polymer from the agent particles 40, forming a fibrin monomer-containing solution which is to be transferred to the syringe 44 in an eighth and ninth step shown in FIGS. 9 and 10, respectively. The separation of the fibrin monomer from the Batroxobin in a liquid 100 produced in the second chamber 34 through the action from the redissolving buffer 88 is simply carried out by any convenient separation process, e.g., through a filtering or preferably a centrifugal separation process or a combination thereof as shown in FIG. 9. The centrifugal separation process is carried out in FIG. 9 through which the agent bodies 40 are separated from the liquid 100 and collected at the inner side surface of the cylindrical wall component 14 of the chamber 34 as the sample container 10 is rotated at a rotational speed which is normally smaller than the rotational speeds at which the sample container 10 is rotated in the separation steps illustrated in FIGS. 3, 4 and 6 as the check valve 58 is not caused to open for providing access through the conduit 65 from the second chamber 64 to the first chamber 32. In FIG. 9, the liquid 98 contained within the first chamber 32 is clearly not exposed to a high gravitational field as the liquid is not on the one hand caused to be separated into liquid components of different densities and on the other hand not shifted from the position also shown in FIG. 8 in which the liquid surface is horizontal.

After the separation of the agent particles 40 from the liquid 100 in a ninth step of the first process shown in FIG. 10 as discussed above with reference to FIG. 9, the liquid 100 is transferred from the second chamber 34 of the sample container 10 to the syringe 44 contained within the third chamber 36 of the sample container by simultaneously raising the plunger body 54 of the syringe 44 and lowering the piston body 22. After the transfer of the fibrin monomer solution to the syringe 44 in the ninth step of the first process shown in FIG. 10, the syringe 44 is removed from the sample container 10 as a unitary structure integrally connected to the tubing 58 through the conical adaptor 56 on which the conical end tube 50 of the syringe 44 is received, as the tubing 58 is of a substantial length as discussed above. Thereupon, the syringe 44 is disconnected from the sample container 10 as the tubing 58 is cut by means of a heating tool simultaneously causing a sealing of the free end of the tubing 58 connected to the conical adaptor 56. Consequently, the conical adaptor 56 serves the additional purpose of providing a sealing adaptor sealing the interior of the syringe 44 relative to the environment as the free end of the tubing connected to the conical adaptor 56 is sealed. After the removal and disconnection of the syringe 44 from the sample container 10, the remaining part of the sample container 10 is disposed and destructed without spilling any liquid constituents from the sample container which constituents might expose the individual or individuals operating the centrifugal separation and processing apparatus on which the sample container 10 is processed to hazardous infection agents as bacteria or vira causing dangerous diseases such as hepatitis or acquired immune deficiency syndrome.

As discussed above, this syringe 44 can be used to coadminister the so-produced fibrin polymer solution with appropriate alkaline buffer or distilled water, preferably with a source of calcium ions, to provide a fibrin sealant to a patient.

The above described sample container 10 and the above described first process of separating a blood sample into specific liquid components and of separating a blood constituent from one of the liquid components may be altered in numerous ways. First of all, the syringe 44 may be omitted as the third chamber 36 of the sample container 10 may constitute a chamber in which the rediffusion buffer is initially contained or supplied to in a step of the first process corresponding to the step shown in FIG. 8 and into which the fibrin containing liquid 100 is later on transferred in a final process step similar to the step shown in FIG. 10.

The separation of the plasma in the step shown in FIG. 6 through centrifugal separation may be substituted by a simple filtering step in which the microporous filter element 74 is simply used for retaining the agent bodies 40 to which the fibrin is linked within the second chamber 34 as the plasma is simply forced back into the first chamber 32. Similarly, the step of filtering the bodies 40 from the liquid 100 as shown in FIGS. 9 and 10 through centrifugal separation may be substituted by a simple filtering separation step in which the microporous filter element 66 is used for retaining the bodies 40 within the second chamber 34 as the redissolving buffer including the fibrin is forced into the syringe 44 or alternatively into the third chamber 36 of the sample container.

Figure 11:
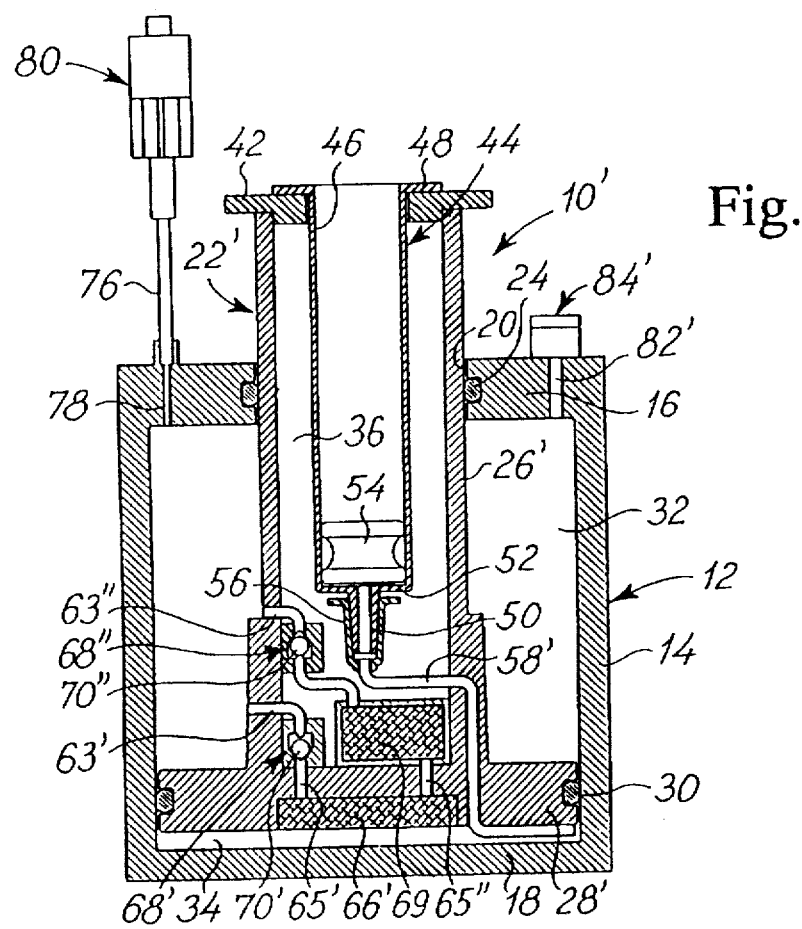
FIG. 11 is a schematic and sectional view similar to the view of FIG. 1 of a second embodiment of a sample container of a centrifugal separation and processing apparatus implemented in accordance with the teachings of the present invention.

In FIG. 11, a second embodiment of a sample container implemented in accordance with the teachings of the present invention is shown designated the reference numeral 10' in its entirety. In FIG. 11 and the FIGS. 12–18 which illustrate specific steps of a second process of separating a blood sample into specific liquid components and of separating a blood constituent from one of the liquid components, when employing the sample container 10' in a second process very much similar to the process discussed above with reference to FIGS. 2–10 components or elements of the second embodiment of the sample container 10' which components or elements are identical to the components or elements described above with reference to FIGS. 1–10 are designated the same reference numerals as used in FIG. 1–10. The second embodiment 10' of the sample container basically differs from the above described first embodiment in that the piston body 22 of the first embodiment 10 is substituted by a piston body 22' of a slightly different configuration and structure. The piston body 22' comprises a cylindrical wall component 26' and a circular plate component 28'. It can also be seen that the cylindrical wall component 26' is recessed slightly at and above the conduit 63' compared to the area of cylindrical wall 26' below the conduit 63'. The shoulder created herein helps keep blood cells out of the conduit 63' during the final stages of separation. Furthermore, the protrusion 38 shown in FIGS. 1–10 can be omitted as the chemical or biochemical agent, e.g., Batroxobin immobilized in Aqarose gel, is provided in a filtering container.

Within the piston body 22' of the second embodiment 10', the syringe 44 is received within the third chamber 36 and communicates with the second chamber 34 of the sample container through a tubing 58' similar to the tubing 58 shown in FIG. 1, however, differing from the tubing 58 discussed above in that the branch piece establishing connection from the tubing 58 to the venting tubing 60 is omitted as the venting tubing 60, the outlet 52 and the filter element of the outlet 52 are omitted. The communication between the first chamber 32 and the second chamber 34 of the sample container 10' is also of a structure somewhat different from the structure discussed above with reference to FIG. 1. The communication including check valves which, however, are caused to open through the generation of a pressure difference and not a gravitational force as a clear distinction from the check valve 68 shown in FIG. 1 and discussed above.

The communication between the first chamber 32 and the second chamber 34 of the sample container 10' includes two conduits. The first conduit includes two conduit segments 63' and 65' and a first check valve 68 interconnecting the conduit segments 63' and 65' and implemented as a ball check valve including a ball 70' and allowing the transfer of liquid from the second chamber 34 to the first chamber 32 and preventing the transfer of liquid from the first chamber 32 to the second chamber 34 through the first conduit. The second conduit includes two conduit segments 63" and 65" and a check valve 68" implemented as a ball check valve including a ball 70" and further a container 69 in which an agent, e.g., Batroxobin is supported on a filter 66". It is to be realized that the inlet of the second conduit from the first container 32 is recessed relative to the outlet of the first conduit 63' provided an annular chamber of somewhat reduced volume communicating with the second conduit exclusively further improving the accuracy of separating the plasma from the blood sample which is introduced into the sample container 10' as will be described below with reference to FIGS. 12–18. The second check valve 68" allows the transfer of liquid from the first chamber 32 to the second chamber 34 and prevents retransfer of liquid from the second chamber 34 to the third chamber 32 through the container 69. The communication to and from the first chamber 32 through the first conduit comprising the conduit segments 63' and 65, through the second conduit comprising the conduit segments 63" and 65" is established through a single microporous filter element 66 which is received within a central recess provided in the circular plate component 28' at the lowest side surface thereof.

The second embodiment 10' of the sample container is like the above described first embodiment 10 of the sample container preferably used for separating a blood sample into blood cells and plasma and further for extracting a blood constituent from the plasma as will be described below with reference to FIGS. 12–18.

Figure 12:
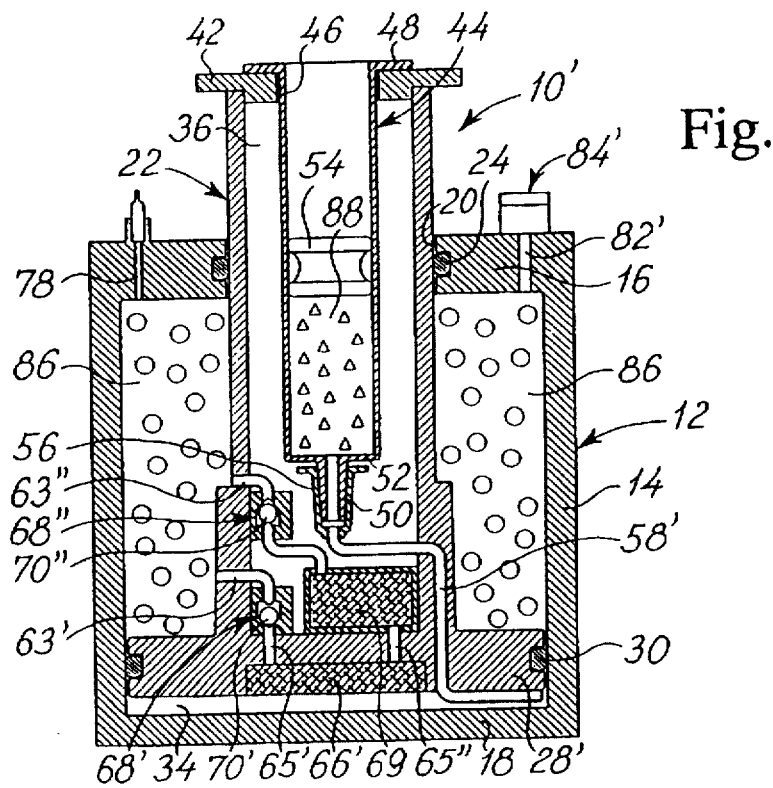
FIGS. 12–18 are schematic and sectional views similar to the views of FIGS. 2–10 illustrating specific steps of a separation and extraction process when employing the second embodiment shown in FIG. 11.

In FIG. 12, a first step similar to the first step described above with reference to FIG. 2 of a second process of separating the blood sample 86 into specific liquid components and of separating a blood constituent from one of the liquid components is shown.

Figure 13:
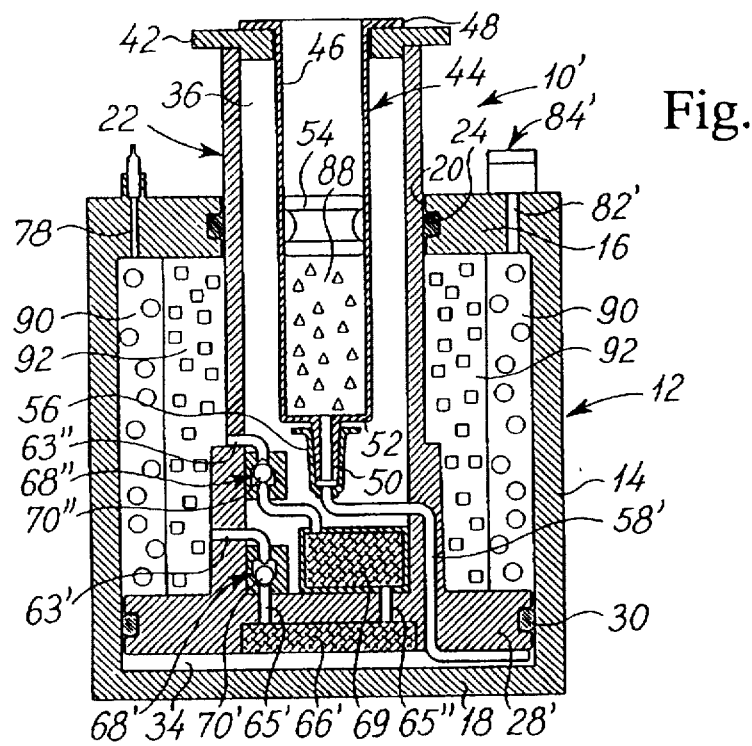

In FIG. 13, a second step of the second process similar to the second step discussed above with reference to FIG. 3 is shown in which second step the plasma 92 is separated from the liquid 90 containing blood cells.

Figure 14:
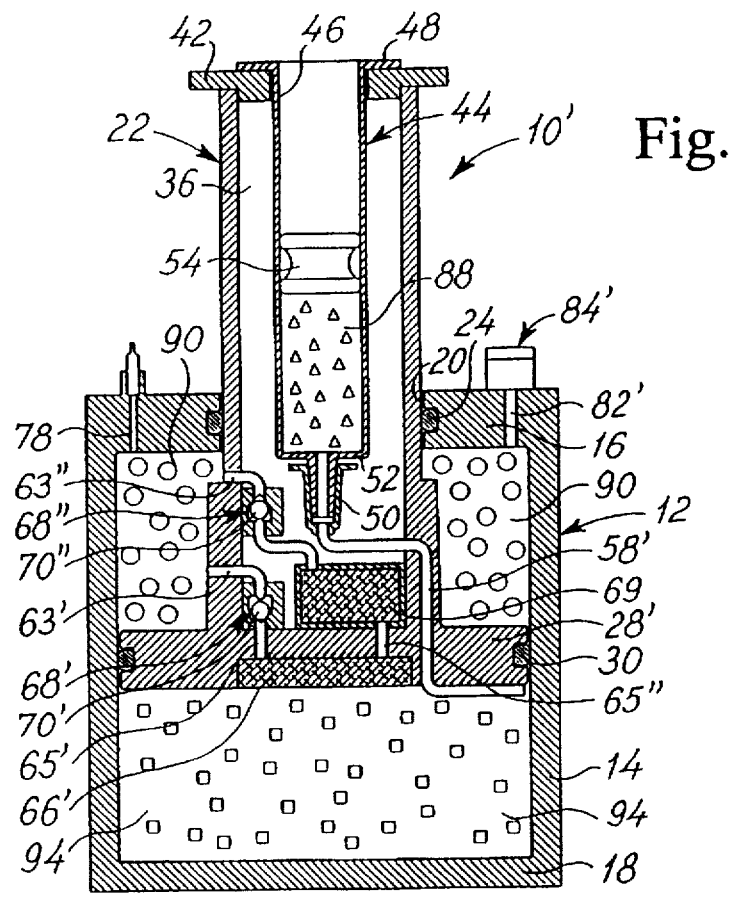

In FIG. 14, a third step of the second process similar to the third step discussed above with reference to FIG. 4 is shown in which third step the plasma 92 is transferred from the first chamber 32 to the second chamber 34 through the second conduit comprising the conduit segments 65" and 63" and further the check valve 68" and the container 69. As the plasma which is transferred from the first chamber 32 to the second chamber 34 is contacted with the Batroxobin contained within the container 69, the plasma contained within the second chamber 34 contains Batroxobin causing the conversion of fibrinogen from the plasma into fibrin monomer which immediately polymerizes into a non-crosslinked fibrin polymer gel. The transfer of the plasma from the first chamber 32 to the second chamber 34 has to be performed at a fairly low speed in order to allow the plasma to react with the Batroxobin contained within the container 69. It should be understood that the speed with which this transfer is made should correspond to the time necessary for the batroxobin or other chemical agent to react with or treat the fibrinogen within the plasma.

Figure 15:
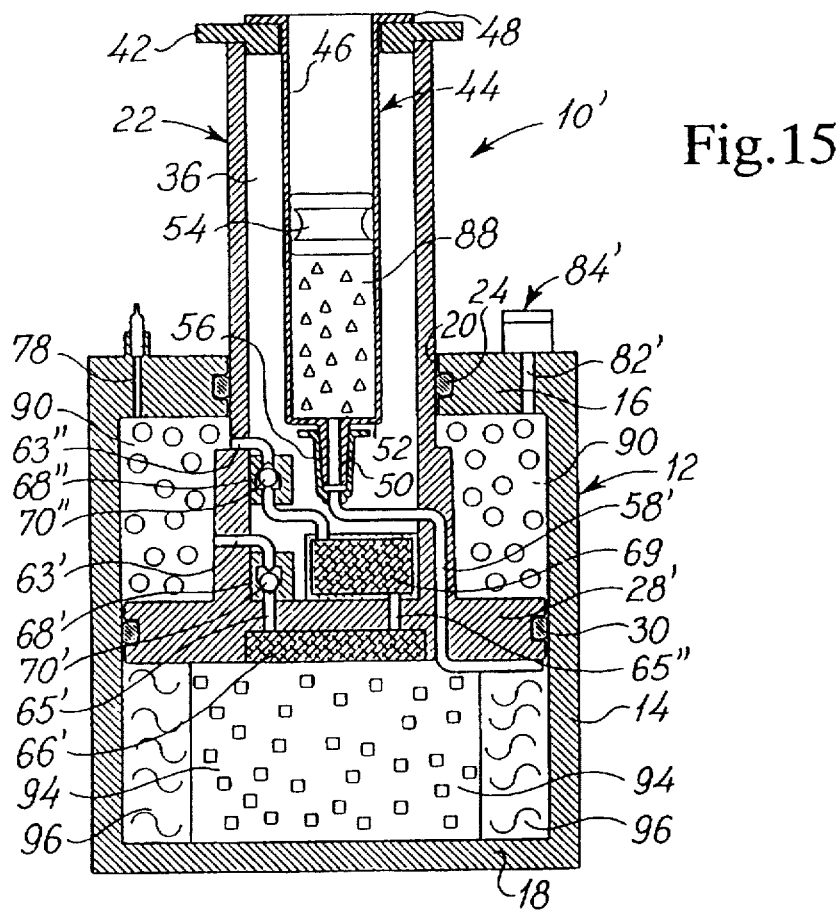
Figure 16:
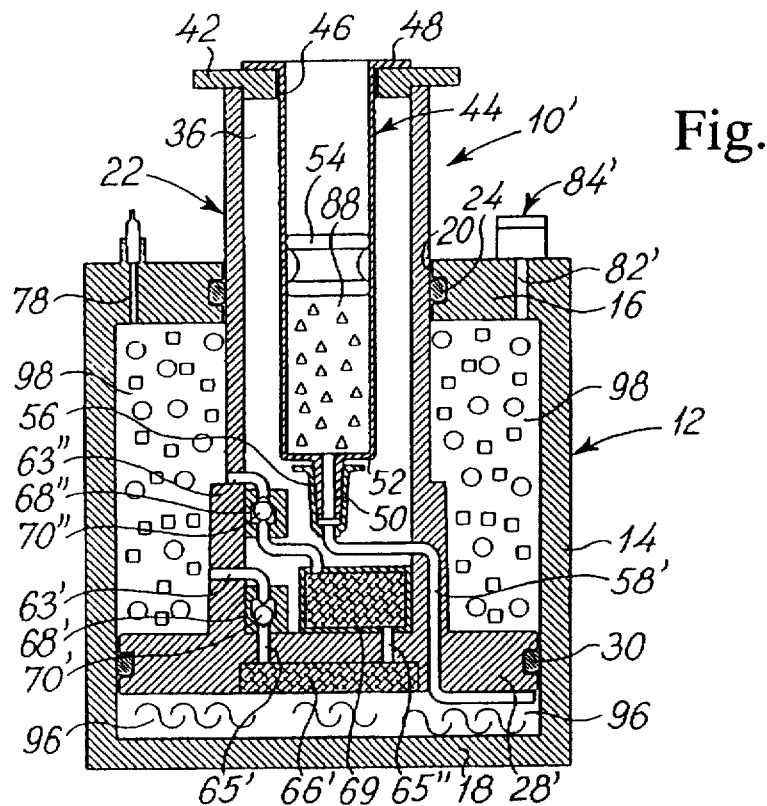

After the transfer of the plasma 94 to the second chamber 34, and optionally after a specific reaction period in which linking of fibrin gel is formed the sample container 10' may be rotated or may be stopped, the fibrin gel is separated from the remaining plasma liquid 94 and agent bodies 40 and in a fourth and fifth step of the second process shown in FIGS. 15 and 16, respectively, corresponding to the fifth and sixth step, respectively, of the second process discussed above with reference to FIGS. 6 and 7, respectively. The plasma 94 contained within the second chamber 34 of the sample container 10" is transferred from the second chamber 34 to the first chamber 32 through the first conduit comprising the conduit segments 63' and 65' and the check valve 68' whereas the check valve 68" prevents that the plasma 94 is transferred through the second conduit.

Figure 17:
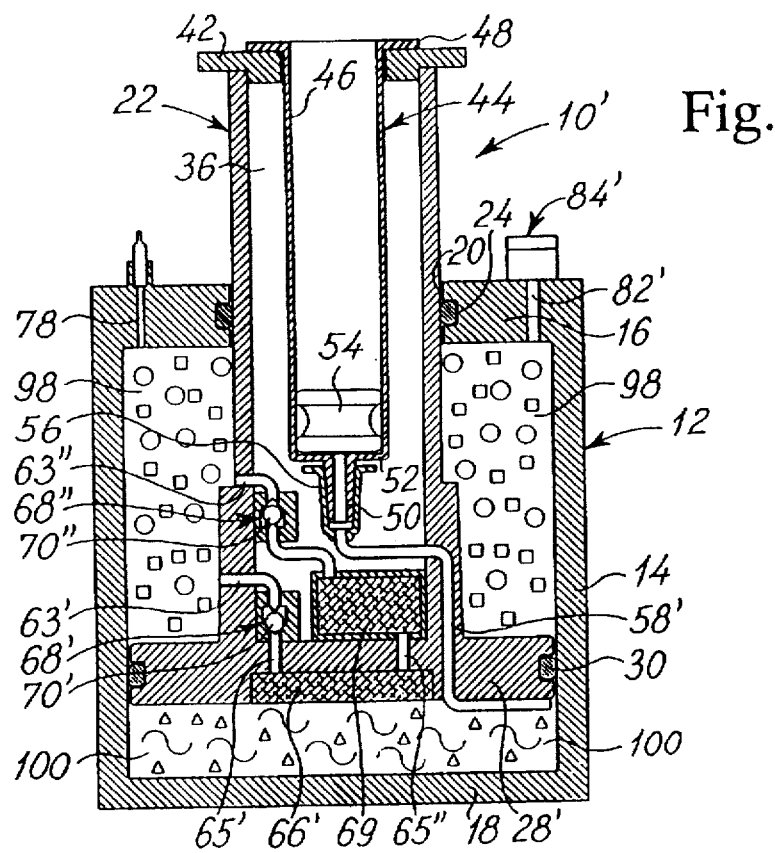

In FIG. 17, a sixth step of the second process is shown in which step the redissolving buffer 88 is transferred to the fibrin containing liquid 100 by simply expelling the redissolving buffer 88 from the syringe 44 in a manner similar to the step discussed above with reference to FIG. 8.

Figure 18:
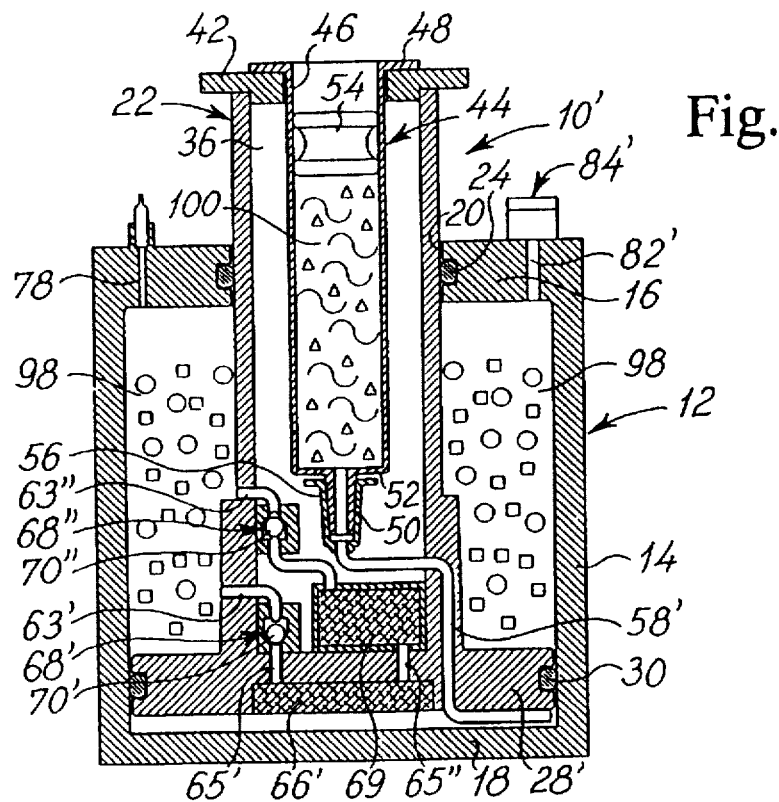

The second process of separating the blood sample into specific liquid components and of separating a blood constituent, the fibrin of the blood sample from one of the liquid components when employing the sample container 10' is finalized in a seventh step of the second process shown in FIG. 18 and corresponding to the ninth step shown in FIG. 10 by transferring the fibrin-containing liquid 100 from the second chamber 34 of the sample container 10' to the syringe 44 contained within the third chamber 36 of the sample container by simultaneously raising the plunger body 54 of the syringe 44 and lowering the piston body 22'. Alternatively, the transfer of the liquid 100 from the second chamber 34 of the sample container 10' to the syringe 44 may be controlled by detecting the force which is used for moving the circular plate component 28' relatively to the housing 12 of the sample container 10' as described above with reference to the first embodiment of the sample container implemented in accordance with the teachings of the present invention.

Like the first process described above with reference to FIGS. 2–10 and the first embodiment of the sample container described above with reference to FIG. 1, the second process described above with reference to FIGS. 12–18 and the second embodiment of the sample container described above with reference to FIG. 11 may be altered and modified in numerous ways, e.g. as discussed above. It is further to be realized that the first and second embodiments 10 and 10' described above with reference to FIGS. 1–10 and 11–18, respectively, may further be modified by simply turning the sample containers upside down in which case the second chamber 34 is positioned above the first chamber 32 and above the third chamber 36.

Figure 19:
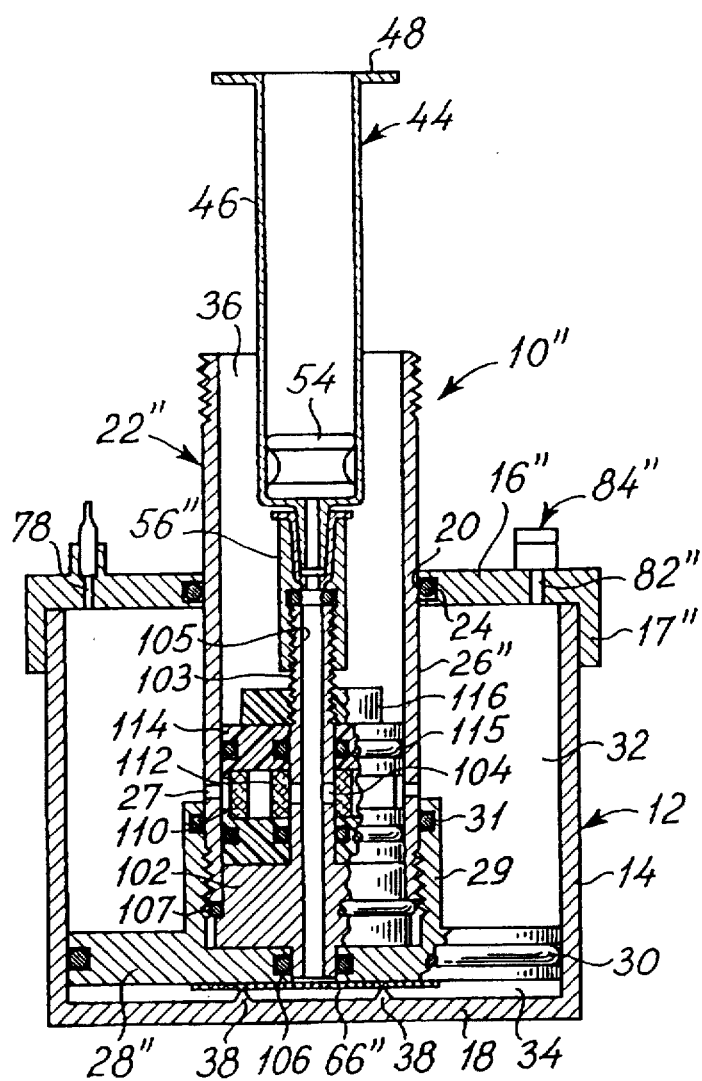
FIG. 19 is a schematic and sectional view of a third embodiment or a prototype embodiment of a sample container of a centrifugal separation and processing apparatus implemented in accordance with the teachings of the present invention.

In FIG. 19, a third embodiment of the sample container is shown constituted by a prototype embodiment. The third embodiment of the sample container is designated the reference numeral 10" in its entirety. The sample container 10" is of a structure basically identical to the structure of the first and second embodiments 10 and 10' described above with reference to FIG. 1 and 11, respectively. In FIG. 19, components and elements which are identical to components and elements described above with reference to FIG. 1 and 11 are designated the same reference numerals as used in FIGS. 1 or 11. The housing 12 of the third embodiment 10" differs from the housing 12 of the first and second embodiments 10 and 10', respectively, in that the top wall component 16" of the third embodiment comprises a skirt part 17" which circumferentially encloses the circumferential wall component 14 establishing a sealed connection to the outer side surface of the cylindrical wall component 14. Through the top wall component 16", the bore 78 extends together with an additional conduit or bore 82" which constitutes a venting conduit similar to the conduit 82' described above with reference to FIG. 11 and communicating with a venting outlet 84" similar to the venting outlet 84' shown in FIG. 11. Alternatively, the venting outlet 84" may be closed by means of a closure or sealing cap, not shown on the drawings. Within the interior of the housing 12, a piston component 22" serving the same purposes as the piston components 22 and 22' described above with reference to FIGS. 1 and 11, respectively, is received and sealed relative to the top wall component 16 through the O-ring sealing 24 which seals against the peripheral outer wall of a cylindrical wall component 26" of the piston component 22". The cylindrical wall component 26" constitute a length of a tube which is provided with outer threads at opposite ends for establishing connection to a top flange component serving the purpose of supporting the flange 48 of the syringe 44 which top flange component is not shown in the drawings and of meshing with interior threads of a cylindrical connection piece which is integrally connected to a circular plate component 28" similar to the circular plate components 28 and 28' described above with reference to FIGS. 1 and 11. The junction between the cylindrical connection piece 29 and the cylindrical wall component 26 is sealed by means of an O-ring sealing 31.

Below the lower side surface of the circular plate component 28", a microporous filter element 66" is arranged constituted by, for example, a piece of conventional cheese cloth, preferably supported on a microporous filter constituting a composite filter structure. The microporous filter element 66" fulfills the same purpose as the microporous filter element 66' shown in FIG. 11. Through the cylindrical wall component 26", two symmetrically arranged bores 27 extend establishing communication from the chamber 32 circumferentially encircling the cylindrical wall component 26" to the interior of the piston component 22".

At the lower end of the piston component 22", an assembly comprising a set of annular elements and a tubular element is supported within the interior of the piston body 22". This annular assembly, shown here within the piston shaft but able to be located anywhere within this or another centrifuge device, serves the purpose of filtering/chemically treating the liquid component separated in the first chamber 32. Generally, in annular concentric arrangement, this assembly comprises an outermost annular support in body 108, and two annular filters spaced inwardly of the body 108 such that these open annular areas are defined 1) inward of the body 108;
2) inward of the first filter; and,
3) inward of the second filter.

More particularly, the assembly comprises a central component 102 which is integrally connected to a tubular element 103 which is provided with outer threads at the upper end thereof which meshes with similar internal threads of a fitting 56" which serves the same purpose as the conical adaptor 56 discussed above with reference to FIG. 1, vis-a-vis the purpose of receiving and establishing connection to the syringe 44.

The tubular component 103 is provided with a through-going bore 105 and further a transversal through-going bore 104 which is arranged in registration with the through-going bore 27 of the cylindrical wall component 26". The component 102 is fixated and sealed relative to the circular plate component 28" by means of two O-rings 106 and 107. The component 102 further serves the purpose of supporting an annular supporting body 108 which is circumferentially sealed relative to the inner cylindrical surface of the cylindrical wall component 26" by means of an O-ring 109. The supporting annular component 108 supports a set of annular filtering elements 110 and 112 which together define an annular space therebetween. The annular filtering elements 110 and 112 are, as is evident from FIG. 19, arranged in registration with the through-going bores 27 and 104 of the cylindrical wall component 26" and the tubular element 103, respectively. The annular filtering elements 110 and 112 are further supported by an additional supporting component 114 which is provided with a circumferential outer O-ring sealing 115 and which is of a configuration similar to the configuration of the supporting annular component 108. On top of the annular supporting component 114, a spacer element 116 is provided, which spacer element is provided with internal threads meshing with the outer threads of the tubular element 103.

Figure 20:
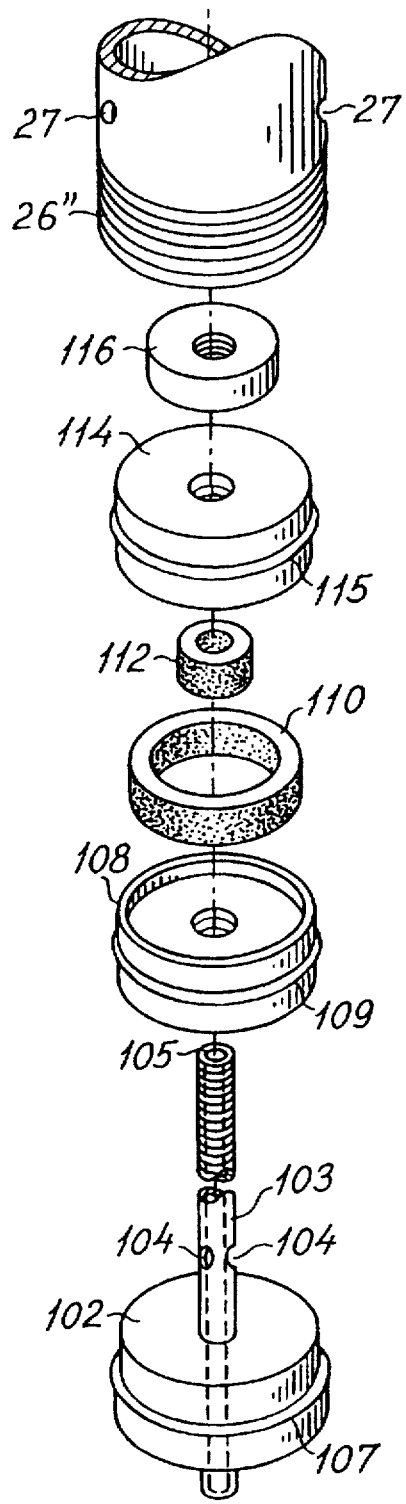
FIG. 20 is a perspective and exploded view of a component of the third embodiment shown in FIG. 19.

The assembly described above with reference to FIG. 19 is shown in exploded view in FIG. 20.

The third embodiment of the sample container 10" shown in FIGS. 19 and 20 is operated in a process similar to the processes described above with reference to FIGS. 2–10 and 12–13 for separating a blood sample into specific liquid components and for separating a blood constituent from one of the liquid components. The blood sample is as discussed above introduced into the first chamber 32 and separated into a liquid containing blood cells and plasma through rotating the entire sample container 10" round the longitudinal axis thereof at a high rotational speed providing centrifugal separation of the higher density blood cells from the plasma. The plasma is transferred from the first chamber 32 to the second chamber 34 by raising the piston component 22" while the sample container is rotated at the high rotational speed causing an initial venting of excess air through the venting outlet 84" and a transfer of the plasma to the second chamber 34 through the through-going bores 27 and 104 of the cylindrical wall component 26" and the tubular element 103, respectively, and the filtering elements 110 and 112 positioned between the through-going bores 27 and 104 and further through the central through-going bore 105 of the tubular element 103 to the microporous filter element 66". The Batroxobin immobilized in the Agarose gels may be enclosed within the space defined between the annular filtering elements 110–112 which consequently constitute a structure having a function similar to the container 69 discussed above with reference to FIG. 11 or alternatively be enclosed within the second chamber 34 and supported on carrier Agarose bodies similar to the agent particles 40 described above with reference to FIGS. 2–10. After the extraction of Fibrin from the plasma, conversion of Fibrin into Fibrin 1, and linking of Fibrin 1 to Batroxobin, the plasma may be retransferred to the first chamber 32 in accordance with the first process described above with reference to FIGS. 2–10 or alternatively be transferred to the syringe 44 through the activation of the plunger 54 causing the plasma to be forced into the interior of the syringe 44.

Figure 21:
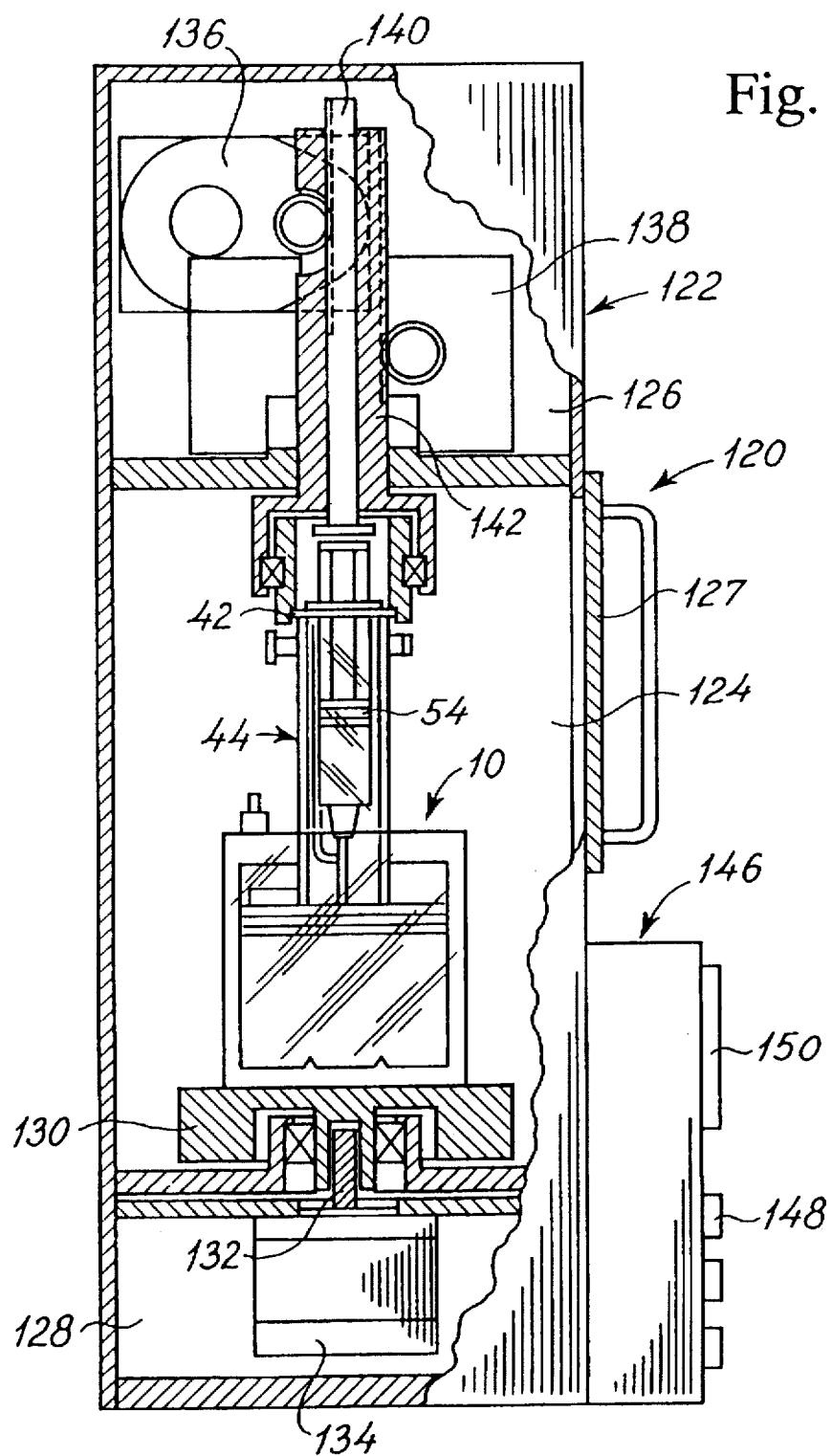
FIG. 21 is a schematic and partly brokenaway view of a centrifugal separation and processing apparatus in which the sample container is received for performing the separation and extraction process in a automatized or semi-automatized manner.

In FIG. 21, an apparatus for receiving the sample container implemented in accordance with the teachings of the present invention and performing the process of separating the blood sample into specific liquid components and of separating a blood constituent from one of the liquid components in an automatized or semi-automatized manner is disclosed and designated the reference numeral 120 in its entirety. The apparatus comprises a housing 122 which is basically divided into three compartments, an upper compartment 126, a central compartment 126 and a lower compartment 128. The compartment 126 is preferably thermostatically controlled to a specific temperature and access to the interior of the compartment 126 for positioning the sample container 10 within the compartment and for removing the sample container and the syringe 44 from the compartment 126 is obtained through an openable shutter or door 127.

Within the central compartment 126, the sample container 10 is received and supported on a rotatable turntable 130 which is journalled on a journalling shaft 132 which constitutes an output shaft of a motor 134 which is housed within the lower compartment 128. The motor 134, consequently, constitutes a means for generating the high rotational speed at which the sample container 10 is rotated in specific steps of the above described process of separating a blood sample into specific liquid components and of separating a blood constituent from one of the liquid components.

In the upper compartment 144, two motors 136 and 138 are arranged cooperating with vertically reciprocating actuator levers 140 and 142, respectively, cooperating with the plunger body 54 of the syringe 44 and the annular lid component 42 of the piston body component 22, respectively.

The apparatus 120 further includes a control section 146 of the housing 122 including an electronic circuitry, preferably a microprocessor controlled electronic circuitry which is operated by means of keys 148 for initiating an controlling the operation of the apparatus 120 for performing the above described process. The section 146 is further provided with a display 150 on which the actual process step and any relevant information such as the duration of the process, the temperature of the second compartment 126 of the housing 122 is presented to an operator. The section 146 is preferably further provided with interface means for interfacing the apparatus with an external computer such as a personal computer and provided with detector means for detecting the overall operation of the apparatus including the transfer of liquid from one of the above described chambers. The detection of liquid transfer may be based on optical detection of conductivity detection involving the detection of constant or varying electric or magnetic fields. The detection of liquid transfer from the first chamber of the sample container to the second chamber of the sample container, from the second chamber of the sample container to the third chamber of the sample container and from the second chamber of the sample container to the first chamber of the sample container may alternatively be based on detection of the force transmitted to the piston component as the force applied to the piston component increases radically as the filter elements through which the liquid is to be transferred are blocked by blood cells or other larger bodies such as the Agarose gel bodies. The above described embodiments of the sample container constituting a separation component in which a blood sample is separated into blood cells and plasma which is further processed for the provision of a Fibrin extract constitutes a component in which a blood sample provided from a patient is simple introduced into a first chamber of the sample container in which the entire separation and processing operations are carried out without the necessity of human contact with the blood sample or constituent thereof eliminating to any substantial extent the risk of exposing laboratory personnel or operators to infectious agents from the blood sample which agents may cause diseases such as hepatitis or acquired immune deficiency syndrome. The Fibrin extract which is produced in accordance with the teachings of the present invention as described above is contained within a syringe which is preferably used in a syringe dispenser of the type described in international patent application, application No. PCT/DK92/00287, international publication No. WO93/06940, in which applicator the fibrin monomer containing liquid contained within the syringe 44 is neutralized through the mixture with a neutralizing agent. The process of separating plasma from a blood sample and of extracting or separating Fibrin from the plasma may e.g. be carried out in accordance with the techniques described in the above mentioned international patent application, application No. PCT/DK87/00117, publication No. WO88/02259 or EP 592,242.

The sample container 10 which is supported on the turntable 130 may preferably be arrested and fixated relative to the turntable 130 by means of arresting or locking components which are shown in greater details in FIGS. 22a, 22b and 22c. The locking components are constituted by a downwardly protruding, circumferential rim part extension 160 of the cylindrical wall component 14 of the housing 12 of the sample container 10. The rim part extension 160 is provided with angularly spaced apart bores e.g. 900 or 1200 spaced apart bores one of which is shown in FIGS. 22a–22c and designated the reference numeral 162. The downwardly protruding, circumferential rim part extension 160 is adapted to be received within a circumferential groove provided in the top surface of the turntable 130. Within a radial bore extending from the outer circumferential rim surface of the turntable 130, two locking pins 166 and 170 are received. The pins 166 and 170 are biased by means of springs 168 and 172, respectively, towards one another and are provided with blunt, conical end parts 167 and 171, respectively, which are contacted with one another at the center of the circumferential groove provided in the top surface of the turntable 130 unless the pins are moved apart as shown in FIG. 22a, as a lower end part 164 of the circumferential, downwardly protruding rim part extension 160 is forced downwardly between the pins 166 and 170 causing the pins to be separated from one another. The pins 166 and 170 and the springs 168 and 172 are arrested within the radial bore of the turntable by means of a sealing plug 174 which is locked in position relative to the circumferential outer rim surface of the turntable 130 by means of meshing threads, or any another appropriate locking structure.

In FIG. 22a, a first step of positioning the sample container 10 relative to the turntable 130 is shown in which step the pins 166 and 170, as described above, are forced apart as the lower end part 164 forces the pins 166 and 170 apart allowing that the lower end part 164 may pass downwardly relative to the pins 166 and 170.

In FIG. 22b, a second step of arresting the sample container 110 relative to the turntable 130 is shown in which step the pins 166 and 170 are forced into contact with one another within the through-going bore 162 of the downwardly protruding rim part extension 160 of the cylindrical wall component 14 of the housing 12. However, the sample container may still be removed from the position shown in FIG. 2b by simply raising the sample container causing the pins 166 and 170 to be separated from one another as shown in FIG. 22a.

The mounting and removal of the sample container relative to the turntable 130 as shown in FIGS. 22a and 22b are accomplished while the turntable 130 is stationary. As the turntable 130 starts rotating propelled by the motor 134 of the apparatus shown in FIG. 21, the pins 166 and 170 are acted upon by a centrifugal force which causes the pins 166 and 170 to be shifted towards a radial offset position shown in FIG. 22c, in which the pin 166 locks within the bore 162 of the rim part extension 160 preventing the housing 12 from being disconnected from the turntable 130 while the turntable and consequently the sample container are rotated at the high and low rotational speeds during the process described above with reference to FIGS. 1–18.

In FIGS. 22d and 22e, two alternative embodiments of optical detector means for detecting the transfer of liquid from the first chamber of the sample container to the second chamber of the sample container are shown. In FIGS. 22d and 22e, the top wall component 16 of the sample container is of a conical configuration connected to an annular wall component within which the cylindrical wall component 26 of the piston component 22 is received and sealed by means of the O-ring 24. The annular wall component 17 is like the cylindrical wall component 26 of the piston component 22 preferably made from a light transparent material allowing the transmission of light through the wall components. In FIG. 22d, the transfer of liquid from the first chamber of the sample container is initiated and the plasma 92 is consequently forced into a narrow annular chamber defined between the outer surface of the wall component 26 of the piston component 22 and the inner surface of the wall component 17. As the transfer of plasma from the first chamber of the sample container proceeds, the liquid 90 containing blood cells is forced into the above described narrow annular chamber as the plasma 92 is transferred from the first chamber of the sample container. The presence of plasma or alternatively blood cells within the narrow annular chamber defined between the outer surface of the cylindrical wall component 26 of the piston component 22 and the inner surface of the annular wall component 17 is detected by means of optical detector means comprising a light generator 180 and an optical detector 188. The light generator 180 is positioned outside the annular wall component 17 and includes a lamp 184 which is connected through an electric wire 182 to the control section 146 of the apparatus 120 shown in FIG. 21. The lamp 184 generates light which is focused by means of the focusing lens 186 providing a substantially parallel light beam 192 which is irradiated to the above described annular chamber and the liquid present within the annular chamber. Opposite to the light generator 180, an optical detector 188 is positioned which is connected to the control section 146 of the apparatus 120 through an electric wire 190. The optical detector 188 receives the light transmitted from the lamp 184 and focused by means of the focusing lens 186 through the above described annular chamber. The light generated by means of the lamp 184 is optionally filtered for providing a substantially narrow light spectrum which exhibit high transmission characteristics through plasma and low transmission characteristics through blood cells in order to improve the detection of blood cells within the annular chamber. The light generator 180 and the optical detector 188 may be supported within the second compartment 124 of the housing 122 described above with reference to FIG. 21 for irradiating light onto the above described annular chamber and for detecting light received from the annular chamber, respectively;

In FIG. 22d, the presence of blood cells within the annular chamber is detected in accordance with the light transmission detection technique. Alternatively, the presence of blood cells within the annular chamber shown in FIGS. 22d and 22e may be detected in accordance with the light reflection detection technique as shown in FIG. 22e.

In FIG. 22e, the light generator 180 and the optical detector 188 are substituted by an integral light generator and optical detector 180' including a lamp 184 similar to the lamp 184 shown in FIG. 22d and an optical detector 188' similar to the optical detector 188 also shown in FIG. 22d. The lamp 184' and the optical detector 188' are connected to the electronic circuitry of the apparatus 120 through electric wires 182', and 190', respectively. The lamp 184' generates a light beam 192' which is irradiated to the annular chamber defined between the outer surface of the cylindrical wall component 26 of the piston component 22 and the inner surface of the annular wall component 17. The wall component 17 is like the wall component 17 described above with reference to FIG. 22d preferably made from a light transparent material whereas the cylindrical wall component 26 may be made from a non-transparent material, e.g.., a light reflecting material. The light irradiated to the liquid present within the annular chamber is partly reflected as indicated by a light beam designated the reference number 194'. The presence of blood cells within the annular chamber is in accordance with the light reflection detecting technique detected provided the light which is irradiated to the annular chamber is partly absorbed by the red blood cells. Thus, the light generated by the lamp 184' is preferably predominant green light which is reflected by the plasma 92 and absorbed by the red blood cells of the liquid 90. On the basis of the shift of the detection signal generated by the optical detector 188', the presence of blood cells within the annular chamber is determined by the electronic circuitry of the control section of the apparatus 120.

EXAMPLE

A prototype embodiment of the sample container implemented as shown in FIGS. 19 and 20 was made from the following components:

The housing 12 of the sample container 10" was constituted by a cylindrical housing component of an inner diameter of 70 mm, outer diameter of 75 mm and a height of 80 mm. The bottom wall 18 of the housing component 12 had a thickness of 2.5 mm. The housing component 12 was cast from polymethylmethacrylate (PMMA). The lid component 17" was cast from POM and had an inner diameter of 75 mm, and outer diameter of 80 mm and an axial height of 13 mm. The piston component 22" was constituted by a circular plate component 28" of an outer diameter of 70 mm–0.1 mm, and a thickness of 7.4 mm. The sealing O-ring 30 was received within a groove of a height of 3.4 mm and a depth of 2.5 mm. The circular plate component 28" was also cast from PMMA. The cylindrical wall component 26" was made from a 100 mm length of a PMMA tube of an inner diameter of 30 mm. The wall component 26" was glued to the circular plate component 28". The body 102, the tube 103, the body 108, the body 114 and the body 116 were all made from PMMA.

At a rotational speed of about 5,500 RPM the concentric separation of plasma and red blood cells can be seen (viewed from top of container as distinct concentric rings) almost immediately, i.e., within the first minute. Over the next minute or two, the platelets can be seen leaving the plasma as is evidenced by the lightening of the color of the plasma. For platelet-free plasma to be collected, the piston should not be raised until this complete separation has occurred. To collect plasma including platelets, the piston should be raised immediately after red blood cell separation but before platelet migration. This is done by a continuous raising of the piston during the platelet separation process. In this way the early portion of the sample collected is high in platelets and the latter portion is low in platelets. Any desired portion of such a sample or the entire platelet containing sample can be utilized as desired. Also, as would be apparent to those skilled in the art, plasma samples with specific platelet contents or specific purities can be collected by varying the speed, time of collection, amount of collection, etc.

In FIG. 23, a diagram is shown illustrating the dependency between the gravitational force generated within the first chamber 32 of the prototype embodiment 10" shown in FIGS. 19 and 20 and described in the above example and the rotational speed at which the sample container is rotated. A curve A represents the gravitational force at the outer wall of the housing 12, i.e. adjacent to the inner side of the wall component 14, and a curve B represents the gravitational force at the outer side of the cylindrical wall component 26" of the piston component 22". It is evident from FIG. 23, that the gravitational force generated within the annular first chamber 32 is represented by the area between the curves A and B and further that the gravitational force at the outer wall component 14 is approximately twice the gravitational force at the cylindrical wall component 26". Thus, a gravitational force varying less than approximately 2 is generated within the annular first chamber 32 as the sample container is rotated.

In FIG. 24, a diagram is shown representing the dependency between the time of rotating the prototype embodiment of the sample container shown in FIGS. 19 and 20 and described in the above example at a rotational speed of approximately 5,500 RPM and the percentage of a blood sample of a volume of 90 ml which has been separated into plasma and blood cells. In FIG. 24, two curves C and D are shown representing the time of separation of the percentage of the blood sample for providing separation of plasma from the blood cells which plasma includes platelets as represented by the curve C and further separating the platelets from the plasma as illustrated by the curve D. From FIG. 24, it is evident that an almost complete separation of the blood sample into blood cells and plasma has been accomplished after approximately 1.5 minutes or even after approximately 1 minute as the blood cells constitutes approximately 15% of the blood sample which part cannot be further separated. Provided the platelets are to be separated from the plasma, a complete separation of platelets free plasma is provided after approximately 3 minutes.

The separation of plasma including platelets from the blood sample is preferably as mentioned above accomplished in a continuous process in which the piston body 22 of the first embodiment 10 or the piston body 22' of the second embodiment 10' is raised continuously in order to continuously transfer the plasma from the first chamber 32 of the sample container to the second chamber 34 of the sample container while the sample container is rotated at the high rotational speed causing the separation of the blood sample into plasma and blood cells. The continuous raising of the piston body is easily controlled by detecting the transfer of plasma from the first chamber to the second chamber based on the above described optical detector techniques or alternatively the detection of the force transmitted to the piston component for raising the piston body. Provided the transfer of plasma from the first chamber to the second chamber is carried out after a complete separation of plasma from the blood sample has taken place, the plasma includes very few platelets and may even constitute plateletfree plasma provided the centrifugal separation has been carried out for an extended period of time, i.e., about 3 minutes, as discussed above.

Figure 25:
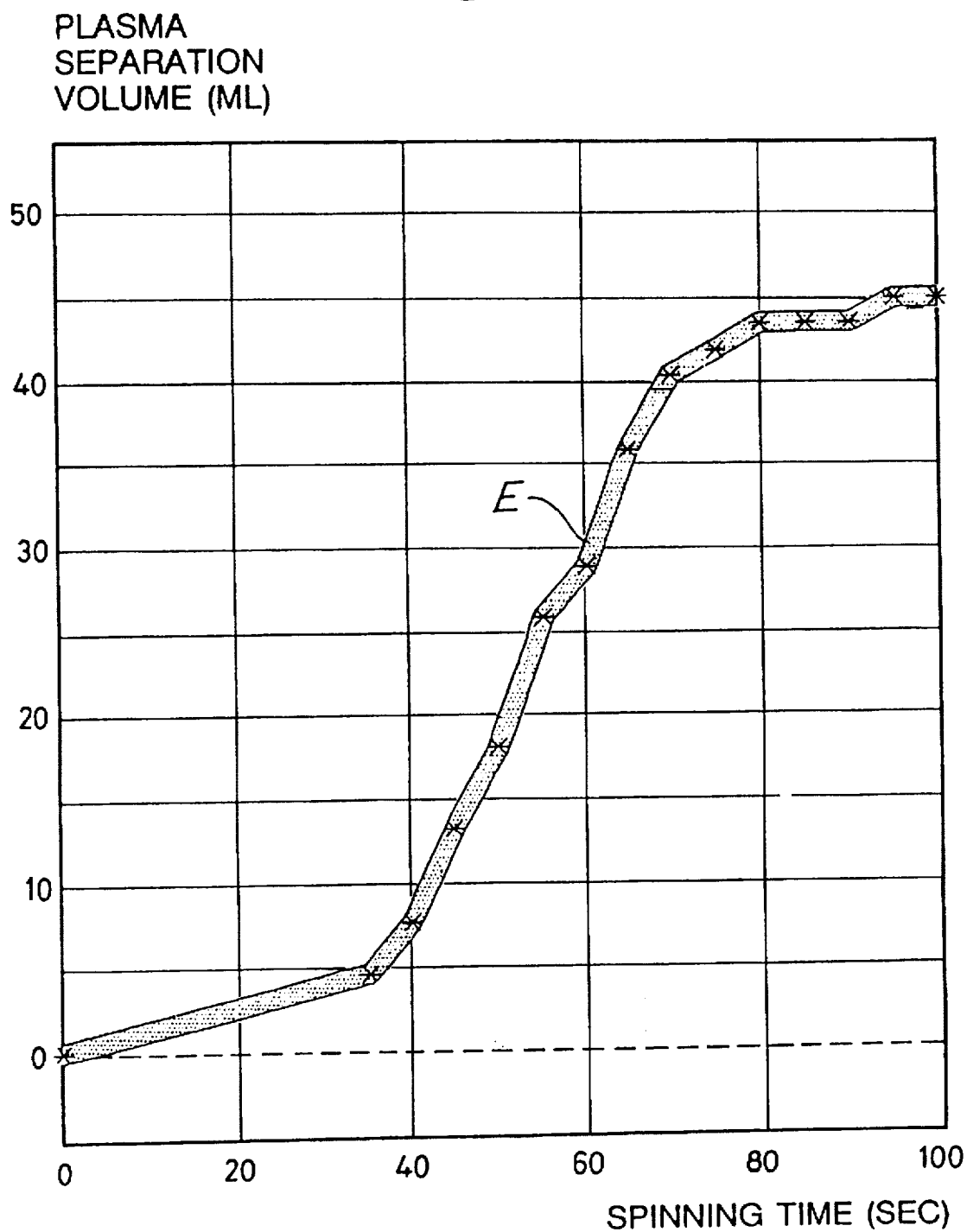
FIG. 25 is a diagrammatic view illustrating the dependency between the volume of a blood sample to be separated by means of the sample container of a centrifuge separation and processing apparatus according to the present invention and the time of performing the separation process.

On the basis of the data represented in FIG. 24, a curve E is illustrated in a diagram shown in FIG. 25 illustrating the time required for accomplishing a complete separation of a blood sample of a specific volume in dependency of the time of rotating the above described prototype embodiment of the sample container at the rotational speed of 5,500 RPM. From FIG. 25, it is evident that within 60 seconds, a 90 ml blood sample may be separated into blood cells and plasma including platelets. A blood sample volume of the order of 100 ml constitutes a maximum blood sample which may be separated by means of the sample container of the above example as the blood sample fills out a majority of the annular first chamber of the sample container. Larger containers, as may be required, can easily be utilized within the scope of the teachings herein.

What is claimed is:

1. An annular assembly locatable within a centrifuge device, for exposing a liquid to a chemical or biological agent during centrifugation comprising, in concentric arrangement, a) an outer annular wall defining an annular outer liquid entry chamber;
   b) a first annular filter disposed inwardly from said entry chamber;
   c) an annular agent chamber containing a source of said chemical or biological agent and disposed inwardly from said first filter;
   d) a second annular filter disposed inwardly from said agent chamber;
   e) an inner liquid exit conduit disposed inwardly from said second filter; and,
   f) pressure means sufficient to provide liquid flow in an inward direction during centrifugation.

2. An annular assembly locatable within a centrifuge device, for exposing a liquid to a chemical or biological agent during centrifugation comprising, in concentric arrangement, a) an outer annular wall defining an annular outer liquid entry chamber;
   b) a first annular filter disposed inwardly from said entry chamber;
   c) an annular agent chamber containing a source of said chemical or biological agent and disposed inwardly from said first filter;
   d) a second annular filter disposed inwardly from said agent chamber; and
   e) an inner liquid exit conduit disposed inwardly from said second filter.

* * * * *